US007261689B2

(12) United States Patent
Holland et al.

(10) Patent No.: US 7,261,689 B2
(45) Date of Patent: *Aug. 28, 2007

(54) PIVOTAL AND ILLUMINATED SAPHENOUS VEIN RETRACTOR WITH TAPERED DESIGN

(75) Inventors: Donna D. Holland, Roswell, GA (US); Douglas G. Evans, Snellville, GA (US)

(73) Assignee: Teleflex Medical Incorporated, Limerick, PA (US)

( * ) Notice: Subject to any disclaimer, the term of this patent is extended or adjusted under 35 U.S.C. 154(b) by 312 days.

This patent is subject to a terminal disclaimer.

(21) Appl. No.: 10/883,664

(22) Filed: Jul. 6, 2004

(65) Prior Publication Data
US 2004/0236185 A1 Nov. 25, 2004

Related U.S. Application Data

(63) Continuation of application No. 10/154,183, filed on May 23, 2002, now Pat. No. 6,805,666.

(51) Int. Cl.
*A61B 1/32* (2006.01)
(52) U.S. Cl. .................. 600/212; 600/215; 600/210
(58) Field of Classification Search ............. 600/185, 600/191, 193, 196, 201, 210, 212, 215, 226, 600/235, 245, 213; 606/190
See application file for complete search history.

(56) References Cited

U.S. PATENT DOCUMENTS

| | | | |
|---|---|---|---|
| 5,913,818 A * | 6/1999 | Co et al. ................. | 600/204 |
| 6,322,499 B1 * | 11/2001 | Evans et al. ............ | 600/212 |
| 6,805,666 B2 * | 10/2004 | Holland et al. ......... | 600/212 |

* cited by examiner

*Primary Examiner*—Cary E. O'Connor
(74) *Attorney, Agent, or Firm*—Baker & Hostetler LLP

(57) ABSTRACT

An illuminated surgical retractor for defining and illuminating a subcutaneous surgical field in the space near a vessel (such as the saphenous vein or radial artery) during a procedure for harvesting the vessel, wherein the illuminated surgical retractor includes a handle member pivotally connected at an acute angle to a first elongate section that has an at least partially tapered width, and includes a second elongate section releasably connected to the first elongate section, wherein a portion of the second elongate section defines an illumination input end portion, which is optically coupled to a light source to substantially illuminate the second elongate section, and further including an insertion area positioned on the proximal end portion of the first elongate section to allow the second elongate section to be inserted into the first elongate section.

31 Claims, 10 Drawing Sheets

PIVOTAL AND ILLUMINATED SAPHENOUS VEIN RETRACTOR WITH TAPERED DESIGN

This application is a continuation of application Ser. No. 10/154,183, filed on May 23, 2002 now U.S. Pat. No. 6,805,666.

BACKGROUND OF THE INVENTION

1. Field of the Invention

The present invention relates to medical devices, and, in particular, to a retractor for harvesting a blood vessel, which, in turn, is used in connection with an ongoing or subsequent surgical procedure. More particularly, the present invention provides such a retractor that is capable of defining and illuminating a subcutaneous working space to ameliorate accessibility to, and to facilitate visualization and harvesting of one or more blood vessels (e.g., saphenous vein) for grafting/transplantation in connection with a surgical procedure (e.g., coronary bypass surgery).

2. Description of Related Art

In certain surgical procedures, it is necessary to remove a portion (or even the entirety) of a patient's blood vessel for use in another, often remotely located part of that, or a different patient's body. For example, it is known to remove/excise some or all of a patient's saphenous vein, cephalic vein, basilic vein, radial artery, or mammary artery for transplantation in connection with a coronary bypass surgical procedure. Once transplanted, the removed section (or entirety) of the vein/artery functions as a graft that replaces both the coronary arteries, which, as a result of aging and/or disease, have become blocked by plaque deposits, stenosis, or cholesterol, thus severely inhibiting their ability to supply life-sustaining blood to the patient's heart.

In some instances, these blockages can be treated with angioplasty, atherectomy or stent placement, and, therefore, coronary bypass surgery is not warranted. Quite often, however, a coronary bypass is required because these treatment methods are either contraindicated, or have proven incapable of removing such blockages from coronary arteries.

According to current coronary bypass surgery techniques, a blood vessel is harvested from elsewhere within a patient's body and grafted into a locus between the patient's aorta and the coronary artery beyond the point of blockage. It is preferred to use a blood vessel taken from the patient undergoing bypass surgery, since he/she is a ready source of suitable vessels that will not be rejected by his/her own body after transplantation.

Currently, the saphenous vein (which is located in a patient's leg) is the most commonly used graft/substitute for small arteries such as the coronary arteries. This is likely because the saphenous vein is typically 3 to 5 mm in diameter (i.e., about the same size as the coronary arteries), and further, because the venous system of the leg is sufficiently redundant, such that following removal of the saphenous vein, other veins that remain within the patient's leg are adequate to provide return blood flow.

Harvesting the saphenous vein entails making one or more incisions in a patient's leg, then using a retractor to reach beneath and lift the skin to expose underlying subcutaneous/connective tissue. This tissue is then pulled away to reveal the saphenous vein, which is then carefully removed.

Although handling of the saphenous vein should be kept to a minimum, it must be separated from the connective tissue, and that requires some contact with the vein. Thus, after the saphenous vein is exposed, medical personnel grasps it with their fingers while stripping off the surrounding tissues with dissecting scissors or other scraping instruments. The medical personnel then uses their fingers and/or blunt dissection tools to separate the vein from the surrounding tissue.

Once the saphenous vein has been completely separated from the surrounding tissue and the tributary veins that feed into the saphenous vein, medical personnel cut the proximal and distal end portions of the vein, and remove the vein from the leg. The saphenous vein is then prepared for implantation into the graft site, and the incision(s) made in the patient's leg is/are closed (e.g., by suturing or with staples).

Until recently, only one incision was made to access the saphenous vein. This incision was quite long—spanning a patient's groin to at least their knee, and often to their ankle.

Making this long, "filet-like" incision inherently presents a serious risk of injury to the medial lymph bundle and/or to nerves located within the patient's leg, as well as a realistic risk of infection to the incision site. Moreover, the healing process associated with this "filet-like" incision is quite protracted (often more prolonged than the healing time associated with the incision(s) made in the patient's chest in furtherance of the coronary bypass) and very painful, especially if the patient has circulation problems in their extremities. Ultimately, in fact, the incision often does not heal properly, and, in such instances, requires medical attention and/or an invasive procedure (e.g., corrective surgery) to enable proper healing thereof.

As indicated in U.S. Pat. No. 6,193,651 to DeFonzo, U.S. Pat. No. 6,228,025 to Hipps et al, and U.S. Pat. No. 6,322,499 to Evans et al., however, techniques now exist that allow the saphenous vein to be harvested by making several small (i.e., about 2.5 inches to 4 inches in length) transverse incisions on the proximal thigh, at the level of the knee joint, and, optionally, at the inner malleolus.

In accordance with these techniques, a retractor is inserted into each of these incisions to define, access and illuminate subcutaneous space. The retractor is used to form a skin bridge to allow for retraction of at least some of the fat and tissue surrounding the saphenous vein, which is then harvested according to, for example, the technique described above, but without the risks/drawbacks associated with making a "filet-like" incision.

Although such risks/drawbacks are avoided by making comparatively smaller incisions in connection with saphenous vein harvesting procedures, some in the art believe that other drawbacks—ones that were not prevalent when saphenous vein harvesting was performed by making the long, "filet-like" incision—can arise by virtue of making these small incisions and/or due to the design of the retractors used in connection with such procedures.

For example, some believe the harvesting process has become complicated by the need to utilize equipment that is small enough to fit into both these small incisions and the subcutaneous space. In particular, they believe that vessel harvesting equipment (e.g., a retractor) should have certain dimensions in order to easily and confidently manipulate a patient's skin and tissue, but also that it is currently not possible for the equipment to have such dimensions, and yet still be able to fit within these small incisions and the subcutaneous space.

One group of patients that would appear to be most affected by these alleged equipment-related limitations are obese patients. Because obese patients tend to have increased quantities of subcutaneous fat and/or tissue in their legs, it is perceived that equipment that is able to fit within small incisions cannot manipulate such fat and tissue to an extent that allows for proper visualization of the subcutaneous space.

Thus, the procedure for harvesting a saphenous vein from obese patients potentially creates a tradeoff that, at least in the minds of some, renders the procedure contraindicated for such patients. This is troubling because it suggests that the obese (who, at present, represent a significant percentage of those who require coronary artery bypass surgery) may have fewer options for vessels that may be harvested for grafting in connection with a coronary artery bypass procedure.

Yet another perceived problem with current techniques for the harvesting of vessels (e.g., the saphenous vein) is that some believe the design of retractors used in connection with harvesting techniques may impede optimal visualization of at least some of the subcutaneous space.

As noted above, such retractors are designed to reach beneath and lift a patient's skin to expose underlying, connective tissue and, in doing so, to create subcutaneous space near the vessel to be harvested.

For example, in furtherance of usage of the retractor (see FIG. 1) described and depicted in U.S. Pat. No. 6,228,025 to Hipps et al. to harvest a patient's saphenous vein, the retractor 210 is grasped at its handle 220, and placed within an incision in a patient's leg in a direction such that the proximal end 211 of the retractor enters the incision (and leg) first, followed by the remainder of its blade sections 230, 240.

Thus, when the retractor 210 is properly positioned beneath a patient's skin, the proximal end 211 of the retractor is located farthest (as compared to the remainder of the blade) from the incision. Once the retractor 210 has been inserted as such, the handle 220 is arched/lifted to, in turn, lift the entire blade, thus defining the subcutaneous space.

As described in U.S. Pat. No. 6,228,025 to Hipps et al., use of the retractor 210 allows for the creation and visualization of enough subcutaneous space to quickly and reliably perform vessel harvesting. Because of the design of the retractor 210, however, the entirety of this subcutaneous space might not be able to be optimally visualized. Most notably, the subcutaneous space defined at or near the proximal end 211 of the retractor 210 may be especially difficult to visualize. This is because the overlying skin and tissue tends to collapse atop and "flap over" the proximal end 211 of the retractor, thus potentially preventing optimal visualization of the area, especially if the patient is obese and, as such, has increased quantities of underlying tissue and/or fat.

Therefore, a need exists for surgical equipment, particularly a retractor, that is able to fit within the small incisions that are made in a patient in connection with minimally invasive vessel harvesting (e.g., saphenous vein or radial artery) and within the subcutaneous space that is defined under the patient's skin, but that also can easily and effectively manipulate a patient's underlying fat and/or tissue (even if the patient has abnormally large quantities thereof, e.g., if the patient is obese) and that can allow for increased visualization of the subcutaneous space defined by the retractor.

SUMMARY OF THE INVENTION

The present invention provides a surgical retractor that meets this, and other needs. As shown in the drawings, the present invention provides a retractor for defining, accessing and illuminating a subcutaneous working space near a blood vessel (e.g., the saphenous vein) located within a patient's body to facilitate safe, reliable and expeditious harvesting of the vessel.

In the contemplated less invasive operation for harvesting a patient's saphenous vein, medical personnel make 2-3 small (i.e., about 2.5 inches to 4 inches in length) transverse incisions on the patient's proximal thigh, at the level of the patient's knee joint and, optionally, at the patient's inner malleolus. This procedure creates/results in several long skin bridges between the incisions. To expose the length of the saphenous vein, which is beneath the skin bridges, the medical personnel lifts the skin and connective tissue with the illuminated retractor.

Once the retractor is positioned as desired, medical personnel may use an existing external retention device to support the retractor and maintain the skin bridge while they dissect connective tissue from around the blood vessel. The external retention device preferably attaches to a structure (e.g., the table on which the patient lies), and is adjustable in order to attach to a connector on the retractor, and to retain the retractor in the desired position.

The illuminated retractor provides a large, well illuminated surgical field, which preferably extends the substantial length of the retractor within the subcutaneous space. With the saphenous vein exposed and visualized, medical personnel use their fingers and/or blunt dissection tools to separate the vein from the surrounding tissues. When the vein has been completely separated from the surrounding tissue and the tributary veins that feed into the saphenous vein have been clipped or cauterized, the medical personnel cut the proximal and distal end portions of the vein and removes the vein from the leg. After vein removal, the 2-3 small incisions made in the leg are sutured or stapled closed, thus completing the vein harvesting procedure.

The illuminated surgical retractor preferably has a handle member, a first elongate section and a second elongate section. The handle member is contoured to be gripped by medical personnel, and, in a preferred aspect of the invention, is pivotally connected to the first elongate section at the distal end portion of the first elongate section to permit one-handed use of the retractor by medical personnel.

Unless indicated otherwise, the term "medical personnel," as used herein, is intended to refer to a single individual that has a role in connection with a surgical procedure. The specific medical personnel who performs a given task in connection with the procedure described herewithin is determined based on the particular task, the level of training required to perform the task, and the availability of other medical personnel.

The handle member permits the retractor to be lifted at any desired angle with respect to the axis of the vessel (e.g., the saphenous vein). Application of a pulling force to the handle member results in a corresponding pulling or retraction force being applied to the skin and/or tissue via the first elongate section. This force, in turn, creates/defines subcutaneous space beneath the skin.

In an exemplary aspect of the invention, an elongated rod portion extends from the handle member. The rod portion allows the retractor to be maneuvered into a desired position by medical personnel, and then fixed in this position by clamping or grasping the retractor with the available operating table retention mechanism(s).

The first elongate section (which is preferably made of a metal or alloy) of the retractor has a first elongate proximal end portion, a first elongate distal end portion, a first elongate outer surface, and a first elongate inner surface, and functions to transfer lifting and/or insertion forces from the handle member to the skin bridge of the patient.

In an exemplary aspect of the present invention, the first elongate section has at least one non-uniform dimensional characteristic, e.g., width. Generally, at least a portion of the width of the first elongate section tapers outwardly at a predetermined inclusive angle of taper. Preferably, the width of both sides of the first elongate section tapers outwardly from approximately its proximal tip to its distal end portion, and/or includes one or more inwardly and outwardly tapering winged/flanged sections.

The non-uniform width of the first elongate section enables the retractor to more easily maneuver and support normal or increased quantities of a patient's underlying fat and tissue, and, therefore, allows for improved visualization of the subcutaneous space defined by the retractor.

The second elongate section, which is preferably made of a transparent material, has a second elongate proximal end portion, a second elongate distal end portion, a second elongate outer surface and a second elongate inner surface, and functions to perform the illumination feature of the present invention.

The second elongate section either has a substantially uniform width (e.g., when the first elongate section includes one or more flanged/winged portions) or a substantially non-uniform width (e.g., when the first elongate section has a tapering width but does not include one or more tapering flanged/winged portions), and is preferably slidable laterally with respect to a portion of the first elongate section and into engagement with the first elongate section such that the first and second elongate sections are substantially adjacent to each other while engaged.

As used herein, reference to the proximal end portion of an element is intended to denote the end portion of an element that is spaced apart from the handle member, and reference to the distal end portion of an element is intended to denote the end portion of an element that is generally adjacent to or closer to the handle member of the present invention.

The first elongate proximal end portion of the first elongate section preferably has a rounded shape or a smoothly radiused pointed shape that allows the retractor to be pushed into any of the transverse incisions. Once so inserted, the retractor can be safely pushed forward underneath the skin, and into/within the connective/subcutaneous tissue.

Additionally, the first elongate proximal end portion of the first elongate section preferably includes an insertion area to receive and retain the proximal end portion of the second elongate section, and to ensure that these sections remain adjacent to each other during the vessel harvesting procedure.

In a preferred aspect of the invention, the insertion area is a substantially U-shaped flap or loop into which the proximal end portion of the second elongate section is laterally, securely insertable.

Although the insertion area should protrude from the first elongate section enough to allow for insertion of the second elongate section therein, it also should provide a low profile extension that does not deter dissection of connective/subcutaneous tissue, and that ensures that the inserted second elongate section will not become dislodged therefrom during the vessel harvesting procedure.

The proximal end portion of the second elongate section preferably has a rounded shape or, alternatively, a smoothly radiused pointed shape. The shape of the second elongate section proximal end portion is selected to allow for insertion thereof into the insertion area of the first elongate section. Its shape also should ensure that the proximal end portion of the retractor (when the first and second elongate sections are connected) can readily penetrate connective/subcutaneous tissue as the retractor is inserted into a small incision and maneuvered into position, and that the proximal end portion of the second elongate section will be securely retained in the insertion area during the vessel harvesting procedure.

Moreover, the proximal end portion of the second elongate section also is preferably configured/shaped to direct light forwardly of the retractor (in addition to the light that emanates from, and extends the substantial length of the retractor) during use to allow for improved visualization of the subcutaneous space in connection with the vessel harvesting procedure of the present invention.

The retractor of the present invention also preferably includes a dissecting tip, which extends from the proximal end portion of the first elongate section. This tip allows medical personnel to use the retractor as a dissecting device while the retractor is being maneuvered into, around and/or through the connective and subcutaneous tissue surrounding the vessel (e.g., saphenous vein). The tip may include serrations thereupon to assist in the dissection of the tissue, and in retaining the retractor in its desired position during the vessel harvesting procedure.

In order to enhance the reflective qualities of the illuminated retractor, the first elongate inner surface of the first elongate section may include a mirrored surface thereon. Also, the second elongate inner surface of the second elongate section may have a machined or molded (e.g., injection molded) micro-lens surface thereon that refracts light forwardly at a desired angle.

In another alternate aspect of the invention, the second elongate inner surface may be reflective, in order to direct illumination outwardly from the second elongate outer surface. Furthermore, the second elongate section may be constructed so as to reflect the illumination forwardly from the second elongate section in order to illuminate the skin bridge forwardly of the illuminated surgical retractor.

For example, the second elongate section may be formed so that the light is transmitted at a forward angle that is preferably between about 15° and 75°, and, more preferably, between about 30° and 60° relative to the second elongate section, and so that illumination may also be scattered to the sides of the retractor as desired.

A preferred form of the retractor also includes a connector, preferably a twist type connector, between the handle member and the first and second elongate sections. This allows for a simple connection (e.g., a one-quarter turn) to reversibly but assuredly secure the first elongate section to the handle with confidence that these components will remain attached as the skin bridge is defined/created and maintained.

The connector also connects the handle member to the second elongate section to ensure that the light energy travels from the light source, through the handle member, and into the second elongate section. The light energy fills the second elongate section such that light energy is radiated from the second elongate section into the subcutaneous space defined by the retractor.

In this manner, light can be provided from the light source via the optical cable to the illumination input end portion of the second elongate section so that the second elongate section is illuminated, thus resulting in an illuminated surgical field.

A further feature of a preferred form of the present invention is that the distal end portion (or heel portion) of the illuminated retractor is formed to shield all nearby medical personnel from the light created by the distal end portion of the second elongate section. Additionally, the first elongate section may include a side channel in a shaft portion thereof to allow a shaft shaped portion of the second elongate section to be inserted therethrough, thus allowing the second elongate section to be replaceably mounted onto the first elongate section as desired.

A further feature of the illuminated retractor of the present invention is that at least a portion of the shaft shaped portion and/or the distal end portion of the second elongate section is preferably spaced apart from at least a portion of the shaft portion and/or the distal end portion of the first elongate section to ensure that there is no heat buildup between these elements of the retractor.

Still other features of a preferred form of the retractor of the present invention are that the light cable passes through the handle member of the retractor, and that a portion of the handle member may be formed to allow the light generated by the light cable to be observed through the body of the handle member. These features enable medical personnel using the retractor to readily determine whether or not the light source for the retractor is in operation.

Additionally, in a further preferred aspect of the invention, the retractor may include a second connection that may be used to connect a standard light cable at the top of the handle member to a shortened light cable in the handle member of the retractor, so that the handle member and elongate members may be packaged and/or sterilized separately. Alternately, the light cable may be allowed to pass through the handle member for direct connection to the light source and the second elongate member as desired.

Still other aspects, embodiments and advantages of the present invention are discussed in detail below.

BRIEF DESCRIPTION OF THE DRAWINGS

For a fuller understanding of the nature and desired objects of the present invention, reference is made to the following detailed description taken in conjunction with the accompanying figures, wherein like reference characters denote corresponding parts throughout the views, and in which.

DETAILED DESCRIPTION OF THE INVENTION

Figure 1:
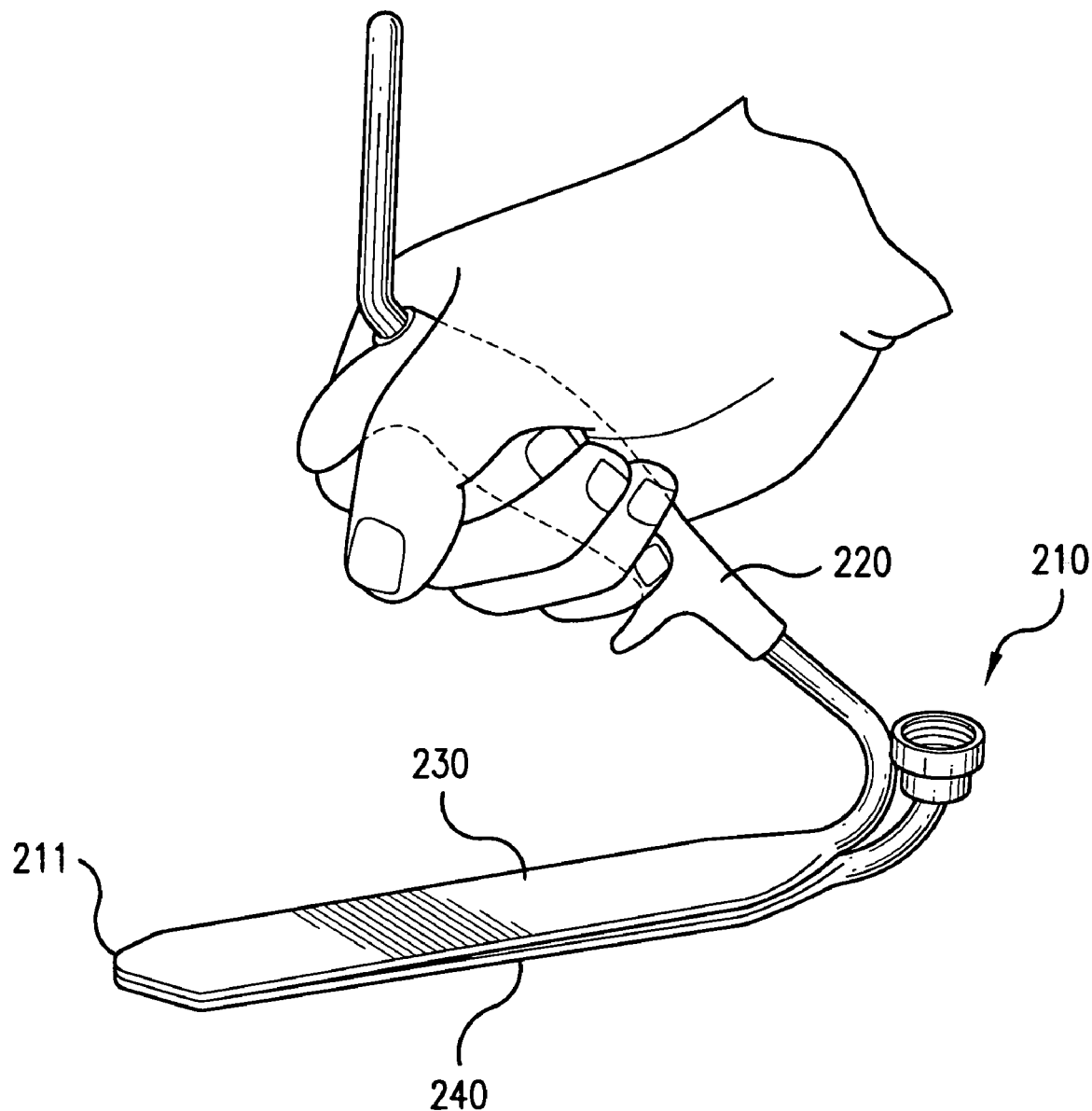
FIG. 1 is a perspective view of a prior art illuminated retractor.
Figure 2:
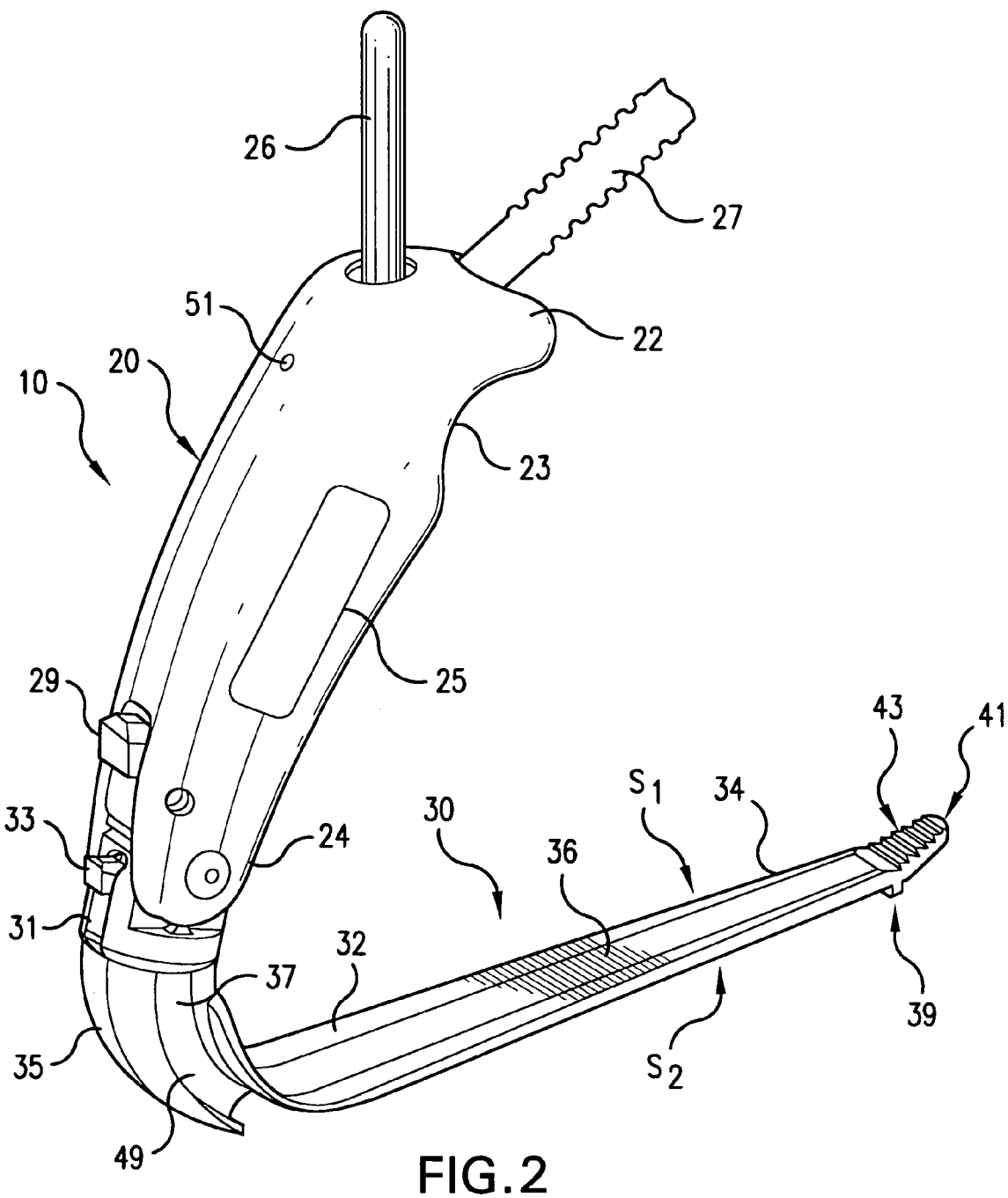
FIG. 2 is a perspective view of a preferred form of an illuminated retractor according to the present invention, wherein the retractor includes a tapering width portion.

The present invention provides an illuminated retractor for assisting in accessing, defining and illuminating subcutaneous space within a patient's body in which a blood vessel (e.g., the saphenous vein) is located, thus allowing for improved visualization of this space, and, in turn, facilitating a procedure wherein the vessel is harvested.

As shown in the drawings, the present invention provides an illuminated surgical retractor 10 having a handle member 20, a first elongate section 30, a second elongate section 40, and a twist connector 31.

The handle member 20 is an elongate and generally cylindrical member that has a first top handle member end portion 22 and a second bottom handle member end portion 24. The second handle member end portion 24 of the handle member 20 is connected to the first elongate section 30 of the retractor 10 at a shaft portion 35 distal to the distal end portion 32 of the first elongate section 30. This connection is made via a twist connector 31 to permit one-handed setup and use by medical personnel.

Figure 3:
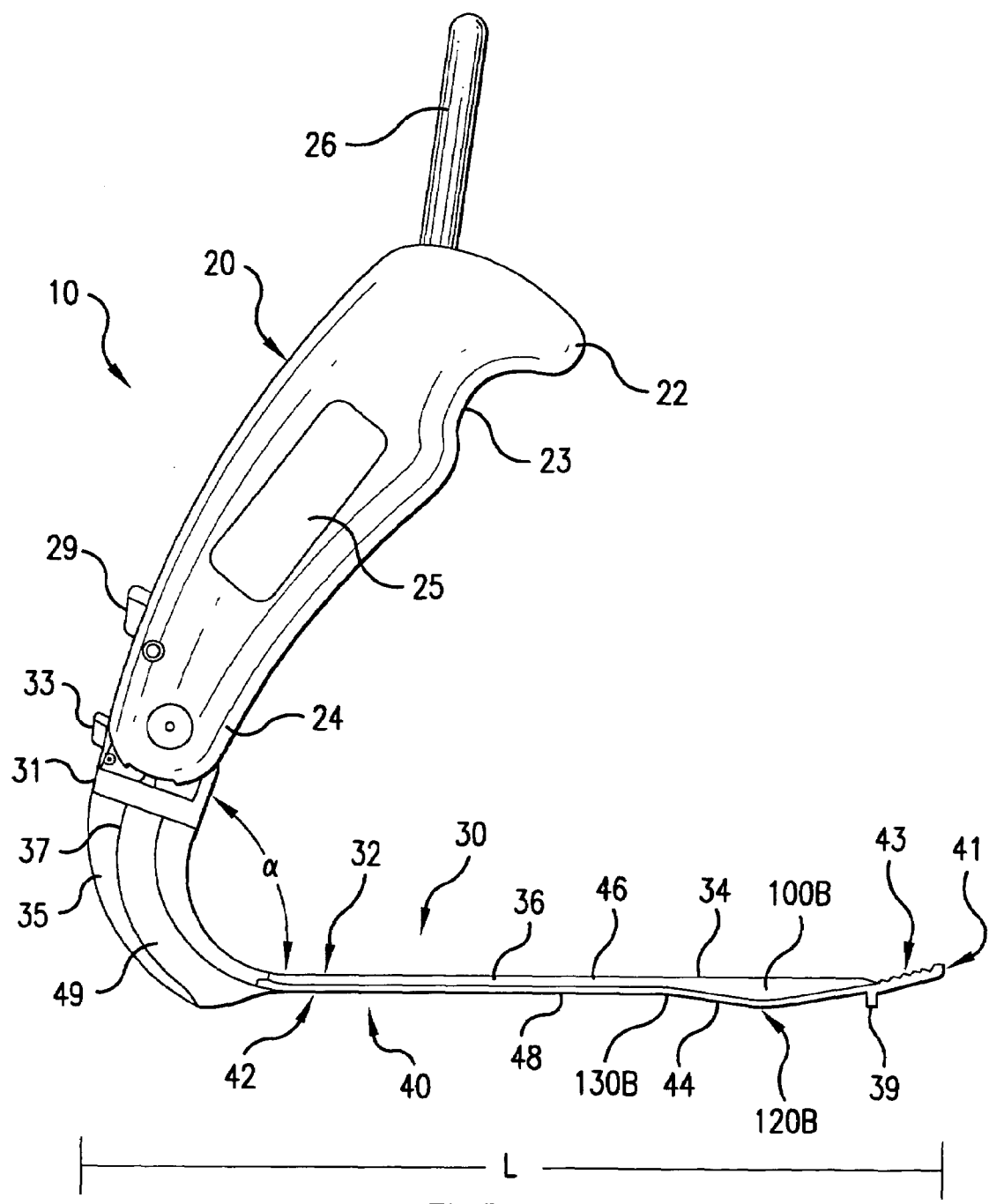
FIG. 3 is an enlarged side view of an alternate embodiment of the retractor of FIG. 2 with the optical cable removed for clarity, and with a first elongate section that includes with a flanged/winged width section.
Figure 4A:
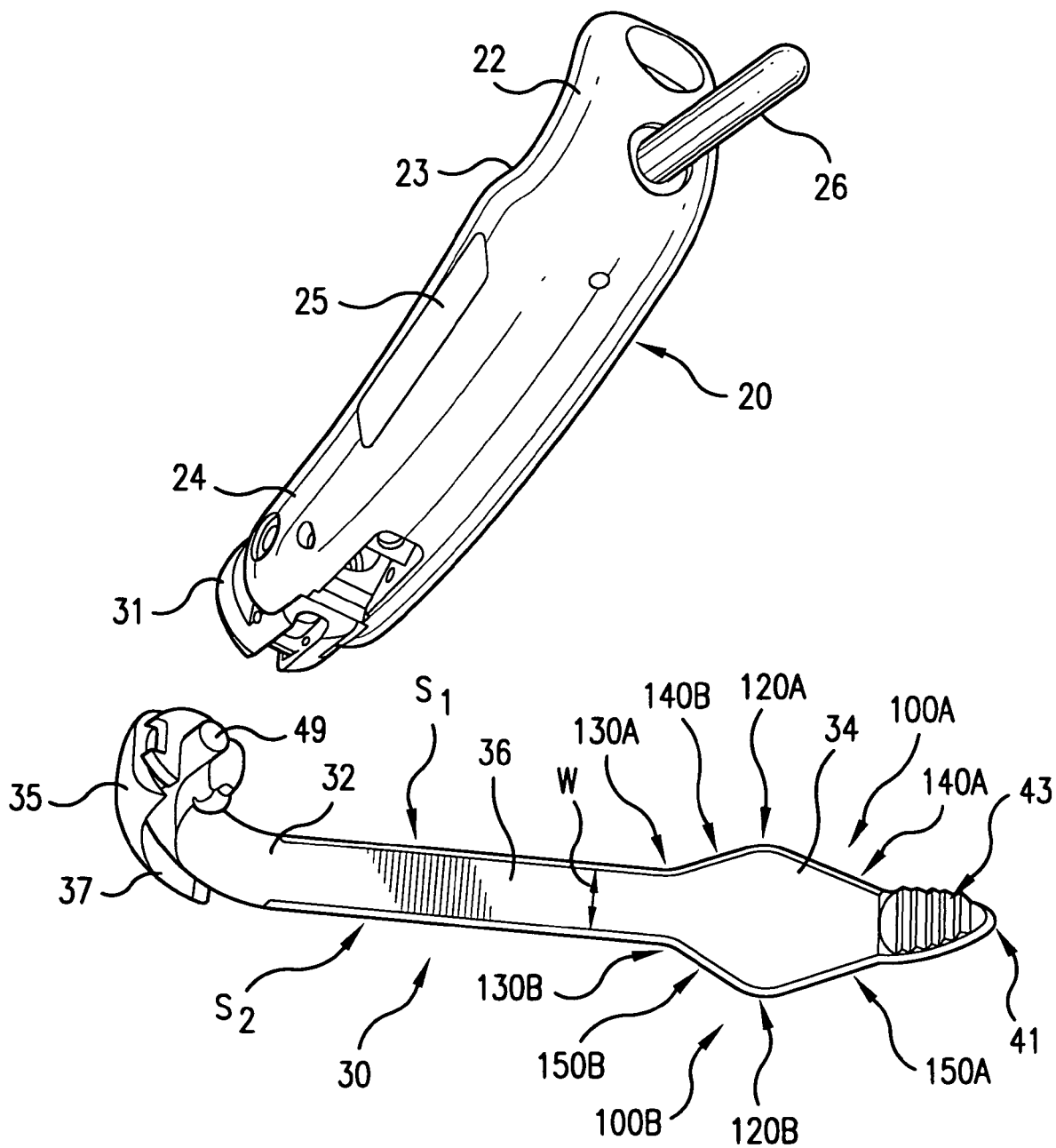
FIGS. 4A and 4B are exploded perspective views of an illuminated retractor according to the present invention showing the handle member separated from the first elongate section and the second elongate section, and with the optical cable removed for clarity, wherein the first elongate section in FIG. 4A includes a flanged/winged portion, and the first elongate section of FIG. 4B has a tapering width.
Figure 4B:
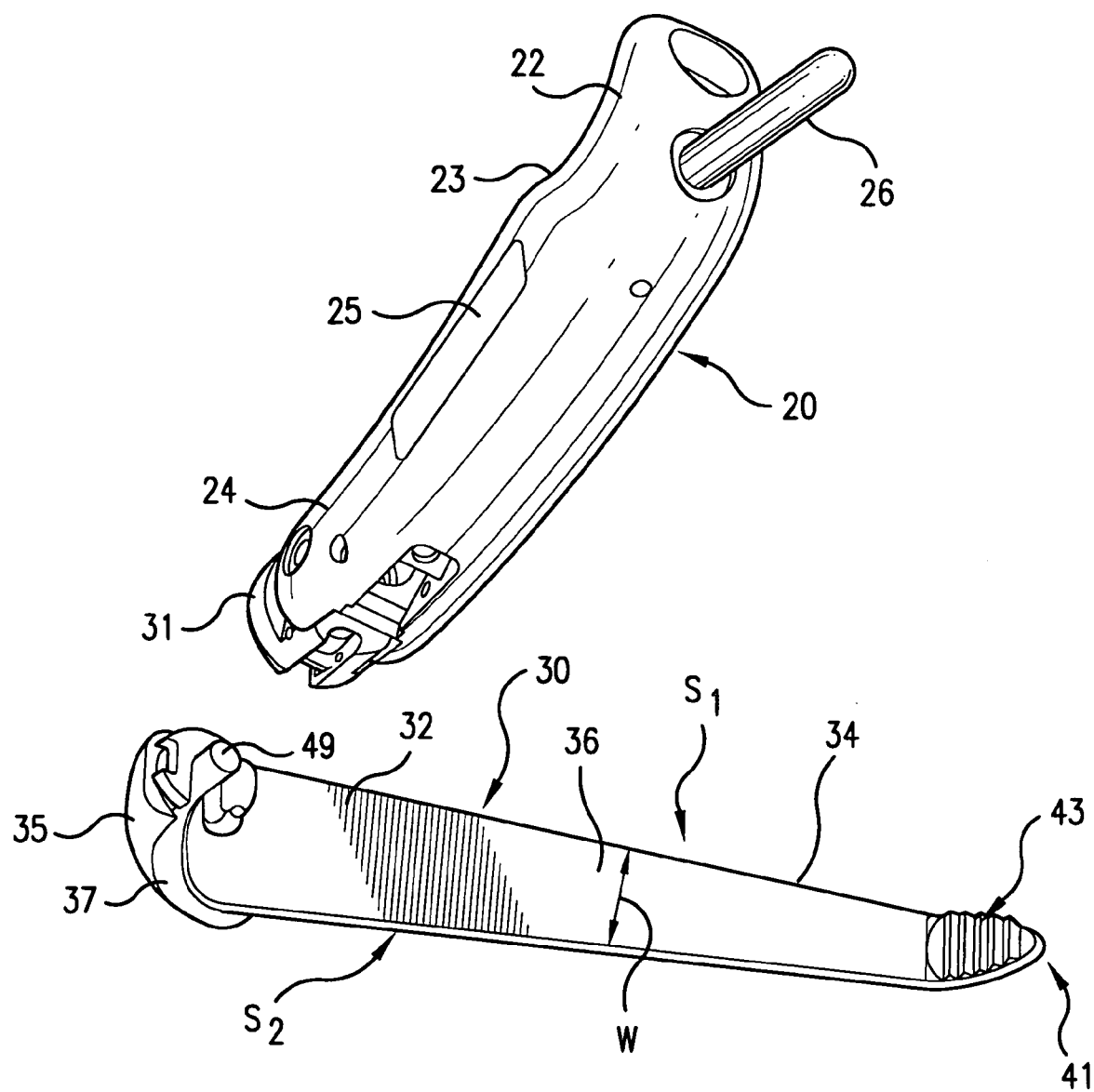
Figure 5:
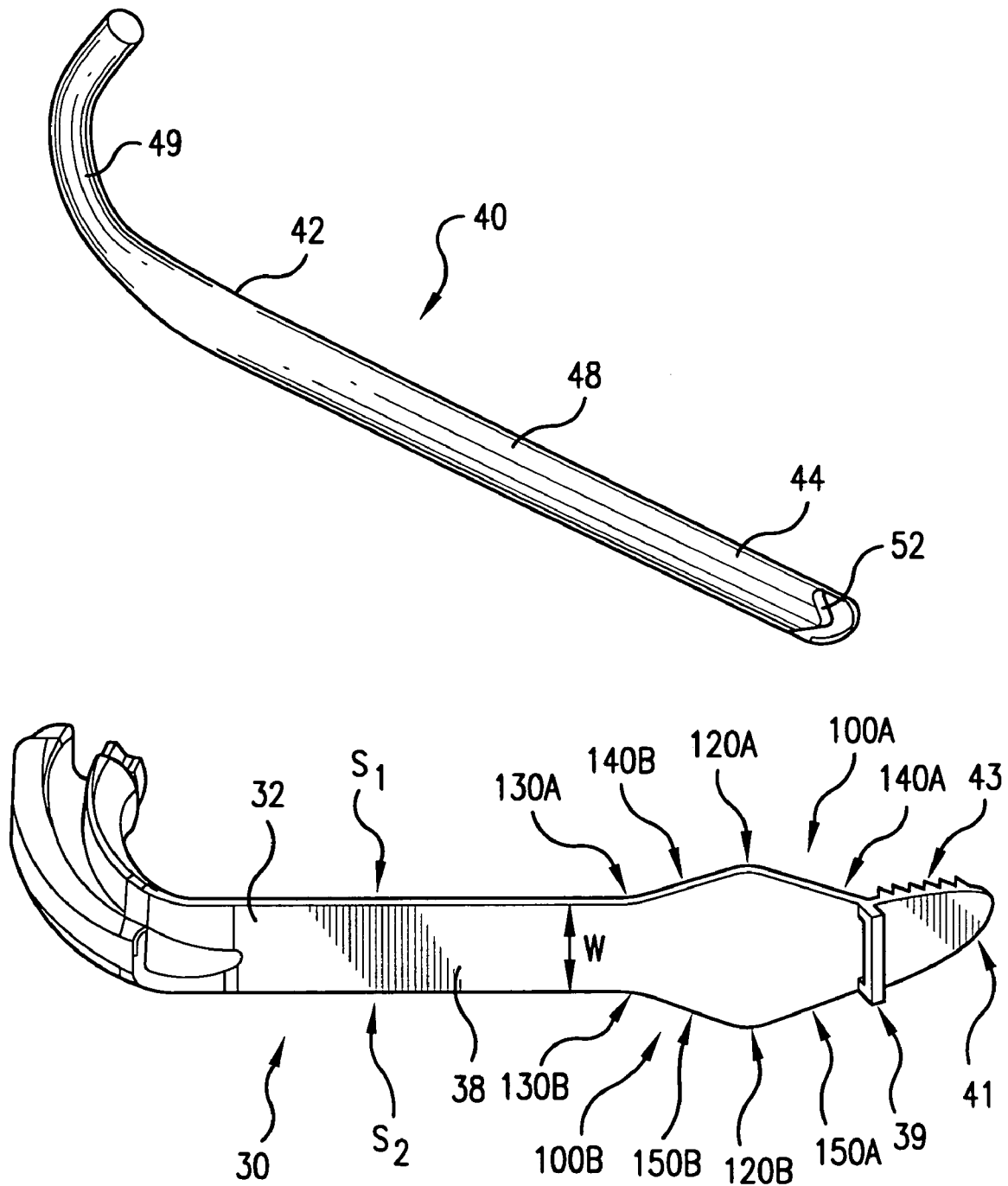
FIG. 5 is a perspective view depicting the relationship between the first and second elongate sections of the retractor wherein the first elongate section includes a flanged/winged portion.
Figure 6A:
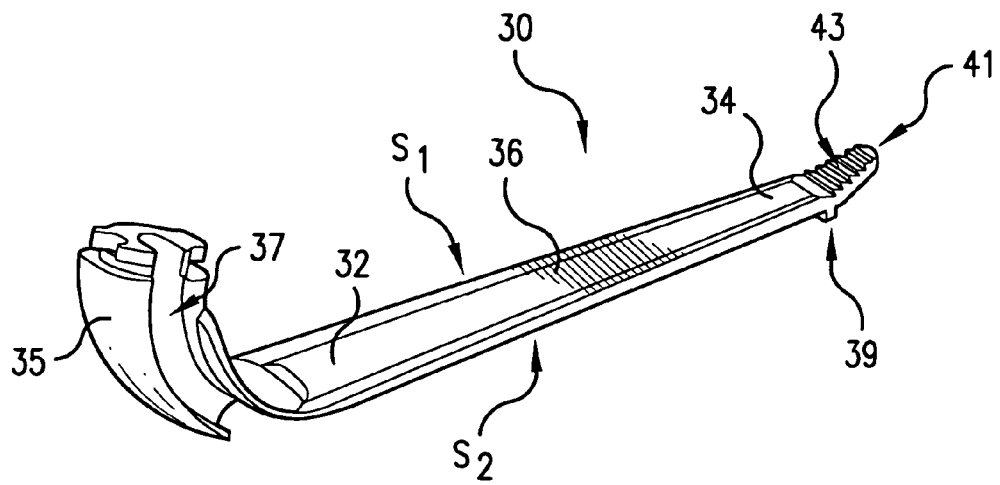
FIGS. 6A-6C are perspective views (FIGS. 6A, 6C) and a front view (FIG. 6B) of a first elongate section of an illuminated retractor according to the present invention, wherein the first elongate section has a tapering width.
Figure 6B:
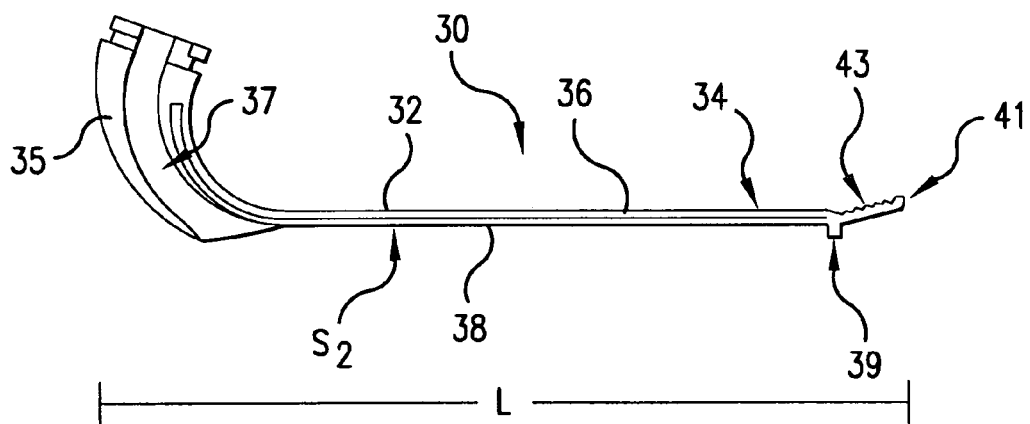
Figure 6C:
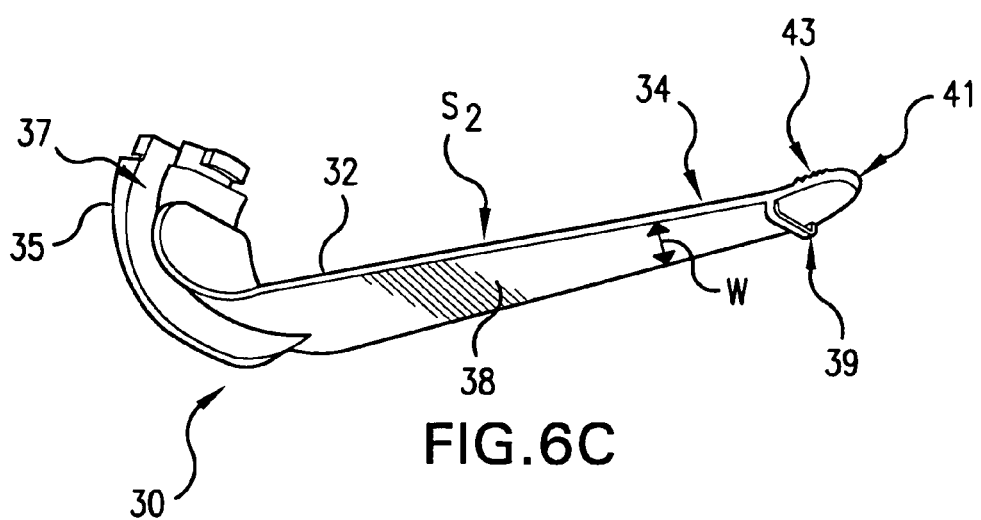
Figure 7A:
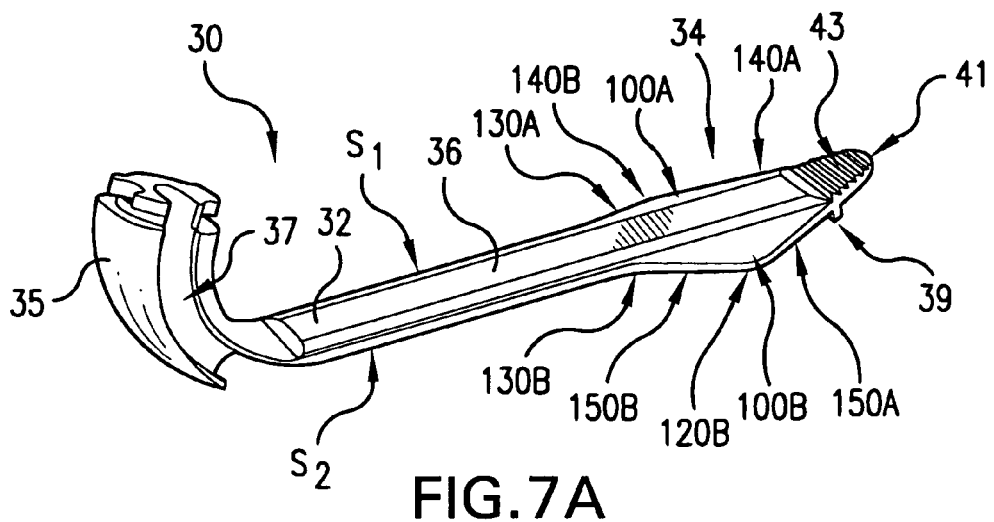
FIGS. 7A-7C are perspective views (FIGS. 7A,7C) and a front view (FIG. 7B) of a first elongate section of an illuminated retractor according to the present invention, wherein the first elongate section includes a flanged/winged portion.
Figure 7B:
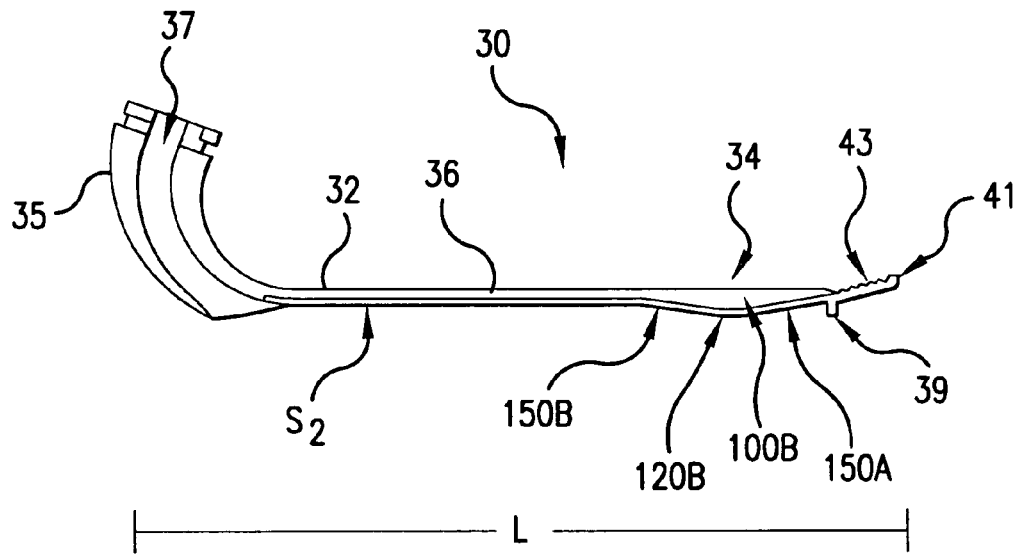
Figure 7C:
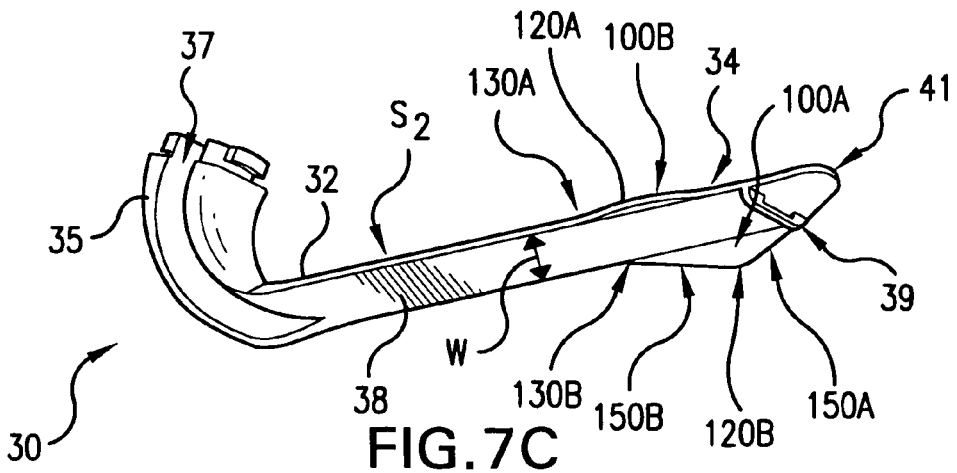

The best combination of retractor mobility and application of retractive or pulling force occurs when an acute angle, $\alpha$, is defined between the handle member 20 and the first elongate section 30. Preferably, this angle, $\alpha$ (see FIG. 3), is between about 30° and 90°, more preferably between about 45° and 75°.

The handle member 20 permits the retractor 10 to be lifted at nearly any angle with respect to the axis of the blood vessel to be harvested. Therefore, when an upward or lifting/pulling force is applied to the handle member 20, a retractive force is applied to the connective tissue (or other body matter) via the first elongate section 30. Such action is effective to create/define subcutaneous space beneath, and a skin bridge above the connective tissue by virtue of the connective tissue and overlying skin being drawn upwardly by the first elongate outer surface 36 of the first elongate section 30 of the retractor 10.

In the context of a saphenous vein harvesting procedure, application of this force causes formation of a skin bridge between the small incision sites. This allows medical personnel access to the underlying connective tissue that surrounds the saphenous vein.

The handle member 20 of the retractor 10 also preferably includes a finger grip surface 23 that is preferably contoured to be gripped by the hand of medical personnel to provide more tactile feel and feedback, and to increase the medical personnel's comfort in using and maneuvering the retractor in connection with the harvesting procedure.

Further, the handle member 20 preferably includes a window area 25 to provide visual confirmation that the light source is operative, and that the retractor 10 is properly set up—that is, when the retractor 10 is illuminated, the window area 25 is illuminated so that medical personnel (and any other people in the surgical suite) will be able to readily determine that the retractor is in use. In a preferred form of the present invention, the illumination of the window area 25 is accomplished by providing a window in the handle member 20 to enable the light generated by the optical cable 27 to shine therethrough as the optical cable extends through the interior of the handle member.

Additionally, the handle member 20 preferably includes a flush port 51 to assist in the cleaning and re-sterilization of the handle member.

The handle member 20 may also have an elongated rod 26 that extends upwardly from the first handle member end portion 22. The rod 26 allows the retractor 10 to be fixed or grasped by various operating table mechanisms (not shown) known in the art, so that the retractor 10 may be fixed in a desired position. These known operating table mechanisms are presently used in the art to support various types of equipment around the surgical field. They are typically attached at one end to the operating table, and include one or more manipulable joints to allow the user to adjust the orientation of a medical device relative to the patient and the operative field.

Use of the operating table mechanism and the elongated rod 26 allows the retractor 10 to be maneuvered into a desired position by medical personnel, and then fixed in that position, thus not requiring any medical personnel to maintain a hold (with either one or two hands) upon the retractor in order to retain it at this desired position.

This, in turn, uncrowds the surgical area both at and near the vessel harvesting site (e.g., a patient's leg in the case of saphenous vein harvesting), and "frees more hands" for performing a variety of tasks relating to the harvesting procedure (e.g., stripping and/or dissecting connective tissue from the saphenous vein).

The first handle member end portion 22 of the present invention also preferably includes an optical cable 27 that extends therefrom. In a preferred form of the present invention, the optical cable 27 is flexible and extends from a twist connector 31 on the proximal portion of the handle member 20 to a conventional light source (not shown).

In an alternate, yet also preferred form of the present invention, the first handle member end portion 22 includes a second connector 54 (see FIGS. 8A and 8B) thereon to allow medical personnel to connect a standard length of optical cable thereto. The optical cable 27 is then connected to a conventional light source. In an embodiment in which two connectors 31, 54 are utilized, the optical cable 27 is connected to a short cable 56 at the second connector 54, and then the second elongate section 40 is connected to the short cable 56 at the twist connector 31.

The second handle member end portion 24 is preferably pivotally connected to the first elongate section 30. As shown, the second handle member end portion 24 preferably includes a depressible pivot knob 29 thereon to actuate the hinge/pivot mechanism located in the interior of the handle member 20.

Depression of the pivot knob 29 enables the user to pivot the first elongate section 30 relative to the handle member 20. When the pivot knob 29 is released, the first elongate section 30 and the handle member 20 are fixedly retained relative to each other.

In a preferred form of the present invention, this hinge/pivot mechanism provides a mechanical joint to connect the first elongate section 30 to the handle member 20. Because the optical cable 27 and/or short cable 56 are preferably flexible, and provide for the transfer of light energy therethrough, the pivoting of the handle member 20 relative to the first elongate section 30 does not affect the connection between the optical cable 27 or short cable 56 and the second elongate section 40.

In a preferred form of the present invention, the twist connector 31 allows for releasable connection of the first elongate section 30 and the second elongate section 40 to the handle member 20 in such a manner so as to allow for the transmission of light through the optical cable 27 and into the second elongate section 40, and so as to provide for the secure attachment between the handle member 20 and the first elongate section 30.

As shown in the drawings, the twist connector 31 preferably includes a key and keyway configuration that allows for the secure and quick connection of the first elongate section 30 to the handle member 20. Additionally, a preferred form of this connection 31 includes the increase in resistance turning of these members, and the secure positioning of the shaft shaped portion relative to the end of the optical cable 27 or short cable 56.

The first elongate section 30 and the second elongate section 40 may be quickly removed from the twist connector 31 on the handle member 20 by depressing the connector knob 33, and then rotating the first elongate section and second elongate section at least one-fourth (i.e., 90°) of a complete (i.e., 360°) turn relative to the handle member 20 to release the keys from the keyway.

Thus, use of the twist connector 31 and the connector knob 33 allows medical personnel to quickly and conveniently attach different first elongate sections 30 and/or different second elongate sections 40 to the handle member 20 as desired.

Although a preferred form of the connector 31 for connecting the handle member 20 and the first elongate section 30 is described herein as a twist connector, it is understood that a variety of connections (including, but not limited to bayonet, snap or threaded connections) may be used instead, provided that the optical cable 27 and shaft shaped member of the second elongate section 40 are securely and operatively connected thereby.

Referring now to the first elongate section 30 of the retractor 10, this section 30 includes a first elongate proximal end portion 34, first elongate distal end portion 32, first elongate outer surface 36, first elongate inner surface 38, and shaft portion 35. Certain portions of the first elongate section 30 resemble those of the first elongate section of the retractor depicted and disclosed in U.S. Pat. No. 6,322,499, but certain other aspects are preferably dissimilar thereto in order to potentially improve the ability of the retractor to define, and enable visualization of subcutaneous space in the context of a vessel (e.g., saphenous vein) harvesting procedure.

The area distal to the first elongate distal end portion 32 of the first elongate section 30 of a retractor of the present invention is generally similar to the comparable area of the retractor of U.S. Pat. No. 6,322,499. For example, as the first elongate section 30 extends distally beyond the first elongate distal end portion 32, the section 30 assumes a generally circular shape to form/define a preferably hollow curved shaft portion 35.

Also, this shaft portion 35 preferably includes a circular bend to form a generally perpendicular or acute angle with respect to the elongate connector and handle member 20. As shown, the shaft portion 35 is also preferably a cylindrical member that includes a side slot 37 that extends lengthwise therealong.

The side slot 37 is formed to receive a portion of the second elongate section 40 laterally inserted therethrough to facilitate/enable the connection of the light source to the second elongate section via the twist connector 31.

Additionally, the outer curvature of the shaft portion 35 functions to shield medical personnel from light emitted from the distal portion of the second elongate section 40, so that the light does not reflect into the eyes of medical personnel during the vessel harvesting procedure.

But unlike the embodiments of the first elongate section of the retractor that are depicted and described in U.S. Pat. No. 6,322,499, in a preferred embodiment of the present invention, both the first elongate outer surface 36 and the first elongate inner surface 38 of the first elongate section 30 of the retractor 10 have at least one non-uniform dimensional characteristic within (and, optionally, beyond) the area between the proximal end tip 41 of the first elongate section and the distal end portion 32 of the first elongate section.

In a preferred embodiment of the present invention, at least a portion of both these surfaces 36, 38, as well as at least some of the area between the distal end portion 32 and proximal tip 41 of the first elongate section 30 of the retractor 10 have widths that are at least partially non-uniform. By way of non-limiting example, the widths of these surfaces 36, 38 and/or this area can be tapered (see FIGS. 2, 4B and 6A-6C) and/or can include one or more tapering flanged/winged sections (see FIGS. 3, 4A, 5, 7A-7C, 8A and 8B).

The first elongate section 30 of the retractor 10 of the present invention may have a range of acceptable dimensions. Generally, the length, L (see FIGS. 3, 6B and 7B), of the first elongate section 30 is in the range of about 3.0 inches to 8.0 inches, preferably in the range of about 4.5 inches to 8.0 inches. A currently preferred length, L, of the first elongate section 30 is about 6.2 inches.

Preferably (but not necessarily), the length, L, of the first elongate section 30 of the retractor 10 is substantially the same whether the first elongate section includes a tapering width and/or one or more tapering flanged/winged sections.

Also, regardless of the taper of first elongate section 30, the width and length of the first elongate section 30 of the retractor 10 should have predetermined relative measurements. For example, even at the maximum and minimum taper points of the first elongate section 30, the width, W, of the first elongate section of a retractor 10 generally will be in the range of about 2% to 50% (preferably in the range of about 15% to 30%, most preferably about 20%) of the total length of the first elongate section.

In an embodiment wherein the first elongate section 30 of the retractor 10 includes a tapered width portion, its width preferably tapers outwardly from approximately the proximal tip 41 of the first elongate section to approximately the distal end portion 32 of the first elongate section—that is, the width of the first elongate section increases from approximately its proximal tip to approximately its distal end portion.

It is understood, however, that the area of the first elongate section 30 that includes a tapering width may be less or more inclusive than the area between approximately the proximal tip 41 and the distal end portion 32. Also, although the first elongate section 30 preferably identically tapers on both its sides $S_1$, $S_2$, it is understood that the amount and/or angle of taper may differ on one or both of its sides.

It is further understood that the retractor 10 may be defined such that only one side ($S_1$ or $S_2$) of the first elongate section 30 is tapered (e.g., wherein one side of the section 30 is substantially straight, while the other side is tapered). Moreover, one of ordinary skill in the art will appreciate that the width of the first elongate section 30 can instead taper inwardly from approximately the proximal tip 41 of the first elongate section to approximately the distal end portion 32 of the first elongate section.

However, as noted above, in a preferred embodiment of the present invention, the width of the first elongate section 30 tapers outwardly from approximately the proximal tip 41 of the first elongate section to approximately the distal end portion 32 of the first elongate section. Such a design/shape enables a retractor 10 of the present invention to be highly effective in manipulating even increased quantities of underlying fat and tissue in furtherance of a vessel harvesting procedure.

This effectiveness is attributable to the fact that the outwardly tapering width of the first elongate section 30 not only allows for increased and/or simplified manipulation of underlying fat and tissue, but also deters the manipulated fat/tissue (even if excessive) from entering the defined subcutaneous space. Specifically, the widened surface area provided by the outwardly tapering width of the first elongate section 30 provides a support, upon which the fat/tissue that is displaced upon being arched/lifted by the retractor 10 to define the subcutaneous space rests, and which, therefore, prevents (or at least impedes) the fat and/or tissue from "flapping over" the sides $S_1$, $S_2$ of the first elongate section 30. And because fat and/or tissue is prevented from "flapping over" as such, visualization of the subcutaneous space is facilitated and, in turn, a vessel harvesting procedure can be performed with potentially increased speed, accuracy and/or reliability, even upon patients with excessive underlying fat and/or tissue (e.g., the obese).

Preferably, in such an embodiment of the present invention, the tapering of the width of the first elongate section 30 is gradual throughout the entirety of the tapered area—that is, it is preferred that the inclusive angle of taper is substantially constant. This ensures that the sides $S_1$, $S_2$ of the first elongate section 30 will not include any jagged portions that could injure the patient, particularly while the retractor 10 is being inserted into or removed from within the incision site(s).

In an exemplary embodiment of the present invention, the inclusive angle of taper of a tapered first elongate section 30 is in the range of about 1° to 75°, preferably about 5° to 60°, most preferably about 9°.

In accordance with such an embodiment, the width, W (see FIGS. 4B and 6C), of the tapered first elongate section 30 is in the range about 0.2 inch to 1.6 inch (preferably about 0.2 inch to 1.3 inch) throughout the entirety of the section 30. Preferably, the width, W, of the tapered first elongate section 30 immediately distal to the proximal tip 41 of the first elongate section 30 is about 25% to 75% (preferably about 30% to 50%, most preferably about 40%) of the width at the distal end portion 32 of the first elongate section 30. For example, the width, W, of the tapered first elongate section 30 preferably is about 0.5 inch immediately distal to the proximal tip 41 of the section 30, and about 1.2 inch at the distal end portion 32 of the section 30.

Even if the width of any portion of the first elongate section 30 of the retractor 10 is 1.6 inch, the retractor 10 can easily fit within any of the small incisions (each of which is about 2.5 inches to 4 inches in length) that are made in a patient's body (e.g., leg) in furtherance of a vessel (e.g., saphenous vein or radial artery) harvesting procedure.

In an embodiment wherein the first elongate section 30 of the retractor 10 includes one or more tapering flanged/winged width sections 100A, 100B, wherein one such section (100A or 100B) preferably is defined on each side $S_1$, $S_2$ of the first elongate section 30.

To define each flanged/winged section 100A, 100B, the width of the first elongate section 30 preferably tapers outwardly (i.e., the width of the first elongate section increases) from approximately the proximal tip 41 of the first elongate section to an area of 120A, 120B of maximum taper. Distal to the maximum taper area 120A, 120B, the width of the first elongate section 30 tapers inwardly (i.e., the width of the first elongate section decreases) until reaching a taper culmination locus 130A, 130B that is distal to the proximal end portion 34 of the first elongate section but proximal to the distal end portion 32 of the first elongate section.

Preferably, the width of each side $S_1$ and $S_2$ of the first elongate section 30 remains substantially constant between this taper culmination locus 130A, 130B and the distal end portion 32 of the first elongate section.

In an exemplary embodiment of the present invention, the maximum taper areas 120A, 120B are located at approximately the proximal end portion 34 of the first elongate section 30. Preferably, the maximum taper areas 120A, 120B are not sharp points, but rather are curved or flat areas in order to lessen the likelihood that the retractor 10 will harm the patient, particularly while the retractor is being inserted into or removed from within the incision site(s).

The flanged/winged sections 100A, 100B include sides 140A, 140B and 150A, 150B, wherein sides 140A, 140B are defined by the outward taper from the proximal tip 41 to the maximum taper areas 120A, 120B, and wherein sides 150A, 150B are defined by the inward taper from the maximum taper areas 120A, 120B to the taper culmination loci 130A, 130B. Thus, the sides 140A, 150A and 150A, 150B of the flanged/winged sections 100A, 100B meet, respectively, at the maximum taper areas 120A, 120B.

Preferably, the tapering of the first elongate section 30 of the retractor 10 is gradual throughout the entirety of the outwardly tapering sides (140A, 150A) and inwardly tapering sides (140B, 150B)—that is, it is preferred that the inclusive angles of taper for both the outwardly and inwardly tapering sides (140A, 150A and 140B, 150B) of the flanged/winged sections 100A, 100B are substantially constant. This ensures that the sides 140A, 140B and 150A, 150B of the flanged/winged sections 100A, 100B of the first elongate section 30 will not include any jagged portions that could injure the patient, particularly while the retractor 10 is being inserted into or removed from within the incision site(s).

The inclusive angles of taper for sides 140A, 150A and sides 140B, 150B are in the range of about 1° to 75°, preferably in the range of about 5° to 60°, most preferably in the range of about 40° to 45°. Generally, the inclusive angle of taper for the outwardly tapering sides (140A, 150A) is slightly greater than the inclusive angle of taper for the inwardly tapering sides (140B, 150B). In a currently preferred embodiment of the present invention the inclusive angle of taper for the outwardly tapering sides (140A, 150A) is about 44°, and the inclusive angle of taper for the inwardly tapering sides (140B, 150B) is about 40°.

The sides 140A, 150A and 140B, 150B can be substantially parallel to the first elongate section 30—that is, the sides of the first elongate section can be in the same horizontal plane as the remainder of the first elongate section. Alternatively, the sides 140A, 150A and 140B, 150B can be curved (i.e., can project upwardly and/or downwardly) with respect to the first elongate section 30. In such an embodiment, each of the sides 140A, 150A and 140B, 150B generally, but not necessarily, will project in the same direction (i.e., either upwardly or, preferably, downwardly) at a predetermined angle (e.g., about 20° with respect to horizontal).

The width, W (see FIGS. 4A, 5 and 7C), of a first elongate section 30 that includes one or more flanged/winged sections 100A, 100B also is in the range about 0.2 inch to 1.6 inch (preferably about 0.2 inch to 1.3 inch) throughout the entirety of the section 30. Preferably, the width, W, of the first elongate section 30 at the taper culmination loci 130A, 130B is about 35% to 85% (preferably about 50% to 75%, most preferably about 60%) of the width at the maximum taper areas 120A, 120B.

Also, the width of the first elongate section 30 preferably remains substantially constant between the maximum taper areas 120A, 120B and the distal end portion 32 such that this portion of the first elongate section is substantially straight/linear. Thus, the width, W, of the first elongate section at the distal end portion 32 also generally is about 35% to 85% (preferably about 50% to 75%, most preferably about 60%) of the width at the maximum taper areas 120A, 120B.

By way of non-limiting example, in a preferred embodiment of the invention, the width, W, of the first elongate section 30 is about 1.3 inch at the maximum taper areas 120A, 120B, and about 0.8 inch at the taper culmination loci 130A, 130B.

Even if the width of any portion of the first elongate section 30 of the retractor 10 is 1.6 inch, the retractor 10 can easily fit within any of the small incisions (each of which is about 2.5 inches to 4 inches in length) that are made in a patient's body (e.g., leg) in furtherance of a vessel (e.g., saphenous vein) harvesting procedure.

Also, the length of the first elongate section 130 proximal to the taper culmination loci 130A, 130B generally is about 15% to 65% (preferably about 25% to 45%, most preferably about 35%) of the length of the first elongate section distal to the taper culimination loci. For example, in a preferred embodiment of the invention, the length of the first elongate section 130 proximal to the taper culmination loci 130A, 130B is about 2.2 inches, and the length of the first elongate section distal to the taper culmination loci is about 4.0 inches.

Although not shown in the Figures, it is understood that a retractor 10 of the present invention may be defined such that only one side $S_1$ or $S_2$ of the first elongate section 30 includes a flanged/winged portion 100 (e.g., wherein one side of the section 30 is substantially straight, and wherein the other side includes the flanged/winged section).

It is further understood that one or both the winged/flanged sections 100A, 100B of the first elongate section 30 of the retractor 10 may have a different shape (e.g., rounded, squared, etc.) than the other, and/or may be defined to affect a different area of the section 30. Moreover, it is further understood that one or both of the sides $S_1$, $S_2$ of the first elongate section 30 may include more than one shaped (i.e., winged/flanged) section 100.

The inclusion of the flanged/winged portions 100A, 100B within the first elongate section 30 of the retractor 10 of the present invention allows for increased visualization of the subcutaneous space (particularly at/near the proximal areas of the retractor) in furtherance of a vessel harvesting procedure, even if the patient has excessive underlying fat and/or tissue (e.g., if the patient is obese).

The widened surface area provided by the winged/flanged sections 100A, 100B of the first elongate section 30 provides a support, upon which the fat and/or tissue that is displaced upon being arched/lifted by the retractor 10 to define the subcutaneous space rests, and which, therefore, prevents (or at least impedes) the fat and/or tissue from "flapping over" the sides $S_1$, $S_2$ of the first elongate section 30. And by preventing the fat and/or tissue from "flapping over" as such, visualization of the subcutaneous space is improved and, in turn, the vessel harvesting procedure can be performed with potentially increased speed, accuracy and/or reliability, even upon patients with excessive quantities of underlying fat and/or tissue (e.g., obese patients).

Also, by defining the flanged/winged sections 100A, 100B at or near the proximal tip 41 of the first elongate section, the retractor is especially better designed to prevent the aforementioned perceived problem of fat and/or tissue "flapping over" the proximal end 211 (see FIG. 1) of known retractors and, thus, impeding visualization of the subcutaneous space near that end of the retractor.

Moreover, still other potential benefits are provided by virtue of the flanged/winged sections 100A, 100B being located at or near the proximal end portion 34 of the first elongate section 30. Such benefits stem from the fact that the retractor 10 is inserted into the patient's body (through the incision) in a proximal-to-distal direction—that is, the proximal tip 41 enters the patient's body first, followed by the flanged/winged sections 100A, 100B, and then the area of the first elongate section 30 located between the flanged/winged sections and the distal end portion 32.

As noted above, the width of the area between the distal end portion 32 of the first elongate section 30 is less than (most preferably about 60% of) the width of the flanged/winged sections 100A, 100B. Such a design allows a retractor 10 that includes a first elongate section 30 with flanged/winged sections 100A, 100B to safely fit into an incision, even if the incision is less than the width of the maximum taper areas 120A, 120B of the flanged/winged sections.

In such an embodiment, the skin surrounding the incision will be temporarily stretched to accommodate insertion of the larger width, flanged/winged sections 100A, 100B. Once those sections 100A, 100B have been advanced into the patient's body (i.e., once the sections have been inserted into and through the incision), the stretched skin will revert to its pre-stretch condition to accommodate insertion of the remaining portions of the retractor 10, each of which has a smaller width than the maximum taper areas 120A, 120B of the flanged/winged sections.

If, instead, the entirety of the retractor was as wide as the maximum taper areas 120A, 120B of the flanged/winged sections 100A, 100B, and if the width of the incision was less than this width, the skin would necessarily remain stretched throughout the entirety of the procedure. This, in turn, could cause the skin to rip/tear, thus causing excess scarring to the patient and/or causing complications to the procedure (e.g., wherein blood from the ripped skin could obstruct the field of vision into the patient's body).

Thus, even if the width of the incision is less than the width of the maximum taper areas 120A, 120B of the flanged/winged sections 100A, 100B of a first elongate section 30 of a retractor, use of such a retractor will still advantageously allow for the aforementioned benefits of added proximal width (i.e., a wider field of view within the patient's body, increased support of a patient's tissue, etc.) without the drawbacks (i.e., ripped/torn skin) that could result if, instead, a greater portion of the first elongate section 30 was wider than the width of the incision.

Although the first elongate section 30 of a retractor 10 of the present invention may include a shroud member as described and depicted in U.S. Pat. No. 6,322,499, it is preferable that it instead include an insertion area 39 in order to receive and retain the proximal end portion 44 of the second elongate section 40, and to ensure that these sections 30, 40 remain adjacent to each other during the harvesting procedure.

In a preferred aspect of the invention, the insertion area 39 is a substantially U-shaped flap or loop into which the proximal end portion 44 of the second elongate section 40 is laterally insertable. Although the insertion area should protrude from the first elongate section 30 enough to allow for insertion of the second elongate section 40 therein, it should provide a tight, low profile extension that does not deter dissection of the tissue, and that ensures that the inserted second elongate section will not become dislodged therefrom during the harvesting procedure.

The insertion area 39 is generally, but not necessarily, formed of the same material as the remainder of the first elongate section 30, which is preferably made of a material that has sufficient strength to assuredly support the skin bridge during use, and that resists degradation, even after repeated sterilization. Exemplary such materials include, but are not limited to, rigid metals or alloys.

The retractor 10 of the present invention also preferably includes a proximal dissecting tip 41, which extends from proximal end portion 34 of the first elongate section 30, and which is preferably at least partially bent. This tip 41 allows medical personnel to use the retractor 10 as a dissecting device while the retractor is being maneuvered into, around and/or through connective tissue. The tip 41 may include (and preferably does include) serrations 43 thereupon to assist in the dissection of the tissue, and to impede unintended movement of the retractor from its desired position during the harvesting procedure.

The second elongate section 40 of the retractor 10 generally is similar to the corresponding section of the retractor described in U.S. Pat. No. 6,322,499 with respect to the materials from which it is made, its function, and the placement of its components. For example, regardless of the design of the first elongate section 30, the second elongate section 40 is preferably made of a transparent material, in order to accentuate its illumination. By way of non-limiting example, the second elongate section 40 may be made of a semi-rigid, transparent material, such as an acryl resin.

In an embodiment in which the first elongate section 30 of the retractor includes one or more flanged/winged sections 100A, 100B, the second elongate section 40 generally is substantially identical in shape to the substantially linear second elongate section that is described in U.S. Pat. No. 6,322,499. The primary reason for this is to allow for economy of parts.

In such an embodiment, the width of the second elongate section 40 preferably (but not necessarily) is substantially equal to or less than the width of the area between the taper culmination loci 130A, 130B and the distal end portion 32 of the first elongate section 30.

In an embodiment in which the first elongate section 30 of the retractor is tapered but does not include one or more flanged/winged sections 100A, 100B, the second elongate section 40 also should include an least partially tapered width. Preferably, in such an embodiment, the second elongate section 40 has a tapered width that is substantially identical to that of the first elongate section 30—that is, the width of the second elongate section 40 is preferably substantially identical to the width of the first elongate section 30.

In an embodiment wherein the first elongate section 30 includes one or more flanged/winged portions 100A, 100B and also is tapered between loci 130A, 130B and distal end portion 32, the second elongate section 40 preferably has a substantially constant, predetermined width, which is less than or equal to the smallest width measurement of the first elongate section between the proximal tip 41 and the distal end portion 32 thereof.

Whether or not the first elongate section 30 is tapered and/or includes one or more flanged/winged portions 100A, 100B, the second elongate section 40 will have a second elongate proximal end portion 44, a second elongate distal end portion 42, a second elongate outer surface 46, a second elongate inner surface 48 and a shaft shaped portion 49.

As the second elongate section 40 extends distally beyond the second elongate distal end portion 42, the second elongate section tapers into a shaft shaped member 49, which then curves to match the curvature and inner dimensions of the shaft portion 35 of the first elongate section 30, and which is receivable through the side slot 37. The tapered aspect of the shaft shaped member 49 of the second elongate section 40 allows the transition between the shaft shaped member and the distal end portion 42 of the second elongate section 40 to be surrounded by the distal end portion 32 and shaft portion 35 of the first elongate section 30, in order to minimize the glare from the shaft shaped member and the distal portion of the second elongate section, and also to protect the shaft shaped member as it curves and extends to the twist connector 31.

Furthermore, the shaft shaped member 49 of the second elongate section 40 is preferably spaced apart from the inner surface of the shaft portion 35 of the first elongate section 30, in order to reduce the potential for the buildup of heat from the light energy passing through the second elongate section.

The second elongate outer surface 46 and the second elongate inner surface 48 correspondingly are eliminated as the second elongate section 40 tapers into the shaft shaped member 49.

The second elongate section 40 may be connected to the first elongate section 30 by inserting the second elongate proximal end portion 44 into the insertion area 39 of the first elongate section. Either while this occurs, or, preferably, thereafter, the second elongate member distal end portion 42 and shaft shaped member 49 of the second elongate section 40 are inserted, respectively, into the shaft portion 35 and side slot 37 of the first elongate section 30. This series of insertions are effective to securely retain the second elongate section 40 adjacent to the first elongate section 30, and to engage the optical cable 27 with the second elongate section through the twist connector 31.

The proximal end portion 44 of the second elongate section 40 may include a chamfered surface 52 (see FIG. 5), which, if included, is preferably at an angle of between about 30° and 60°, and, more preferably, at an angle of about 45°. Although this chamfered surface 52 is illustrated solely in connection with a retractor 10 that includes one or more flanged/winged section 100A, 100B not shown, it is understood that a chamfered surface may be present if such sections 100A, 100B are not present.

The chamfered surface 52 functions similar to a headlight, whereby it projects light from the forward end of the second elongate section 40 and beyond the end of the retractor 10. Therefore, light is preferably passed outwardly from the second elongate section 40 and forwardly from the chamfered surface 52 to illuminate the subcutaneous space defined by the retractor 10.

Alternately, the second elongate section 40 may be connected to the first elongate section 30 in any manner known in the art that is within the level of ordinary skill of one in the surgical field.

For example, although less desirable than the manner of attachment described above, the second elongate outer surface 46 may be chemically bonded to the first elongate inner surface 38 through the use of an adhesive, or by other chemical bonding means known to one skilled in the art.

Such chemical bonding may permanently affix the first and second elongate sections 30, 40 or may preferably allow these elongate sections 30, 40 to be releasably connected to allow for ease of sterilization of the sections. Alternately, if the second elongate section 40 is a light fiber element, the light fiber element may be threaded through various retention members located along the lengthwise dimension of the first elongate section 30.

The second elongate proximal end portion 44 of the second elongate section 40 has a rounded shape or, alternatively, a smoothly radiused pointed shape. The shape of the second elongate proximal end portion 44 is sized to be securely received in the insertion area 39 of the first elongate section such that flexing of any portion of the first or second elongate sections 30, 40 will not separate/free the second elongate section from the insertion area 39.

The first elongate outer surface 36 of the first elongate section 30 preferably has a slightly curved, convex cross-sectional shape. This aids in the prevention of unnecessary trauma to the retracted fat/tissue because the first elongate outer surface 36, which is in contact with the subcutaneous tissue when the pulling force is applied to the retractor 10, presents no sharp edges that could cause accidental tearing of the tissue. This shape also aids in distributing the force applied to the retracted tissue by the first elongate section 30.

The first elongate inner surface 38 of the first elongate section 30 is preferably generally flat in cross section to further reinforce the first elongate section 30. Alternately, the first elongate inner surface 38 may be generally concave in cross-section.

The second elongate outer surface 46 of the second elongate section 40 may also preferably define a generally flat surface in cross-section that is complementary to the preferred cross-sectional shape of the inner surface 38 of the first elongate section 30. As will be obvious to one skilled in the art, if a complementary fit of the second elongate outer surface 46 of the second elongate section 40 and the inner surface 38 of the first elongate section 30 is desired, the outer surface 46 of the second elongate section 40 may have nearly any geometric cross-section that allows the second elongate outer surface 46 to complementarily fit against the inner surface 38 of the first elongate section 30, as there is no requirement that the first elongate inner surface 38 be concave in cross-section.

There is also no constraint requiring that the outer surface 46 of the second elongate section 40 be complementarily shaped to the inner surface 38 of the first elongate section 30. The only constraint on the shape of the geometric cross-section of the second elongate section 40 is that the chosen geometric cross-section should allow the second elongate section 40 to be protected, by means known in the art, by the first elongate section 30 such that the first and second elongate sections 30, 40 are preferably operatively interconnected and complementary to each other. Even more preferably, the first and second elongate sections 30, 40 are substantially parallel to each other, while also providing the optimal and desired illumination in furtherance of the vessel harvesting procedure.

In order to enhance the reflective qualities of the retractor 10, the first elongate inner surface 38 of the first elongate section 30 preferably has a mirrored or reflective surface. Also, the second elongate inner surface 48 of the second elongate section 40 preferably has a machined micro lens surface to refract the light in the desired direction(s). The mirrored surface of the first elongate inner surface 38, and the surface of the second elongate inner surface 48 act to minimize the loss of the light intensity that is provided to the surgical field by the illuminated retractor 10. Additionally, the second elongate section 40 may be formed so as to specifically direct the light forwardly or towards the proximal end of the retractor to, in turn, direct the illumination forwardly beyond the second elongate proximal end portion 44, thereby assisting medical personnel by illuminating the area of interest.

Because the second elongate section 40 of the present invention is readily removable once inserted into the first elongate section 30, it is anticipated that a variety of second elongate sections may be used, including second elongate sections that are formed to direct the illumination forwardly and/or to one or both sides of the retractor 10 as desired and/or as dictated by the nature of the harvesting procedure.

As shown, the illumination from the retractor is preferably at an angle of about 45° forwardly of the retractor 10, although this forward orientation of the light may be oriented to be between 30° and 90° with respect to the lengthwise dimension of the retractor. Similarly, the second elongate section 40 may be formed to direct light sideways from the retractor 10 at an angle of between about 15° and 90°, and, more preferably, about 45° with respect to the retractor 10.

In an exemplary embodiment of the present invention, light energy passes from the light source, through the optical cable 27, and enters the second elongate section 30 of the retractor 10 at the end portion of the shaft shaped member 49 adjacent to the twist connector 31.

Figure 8A:
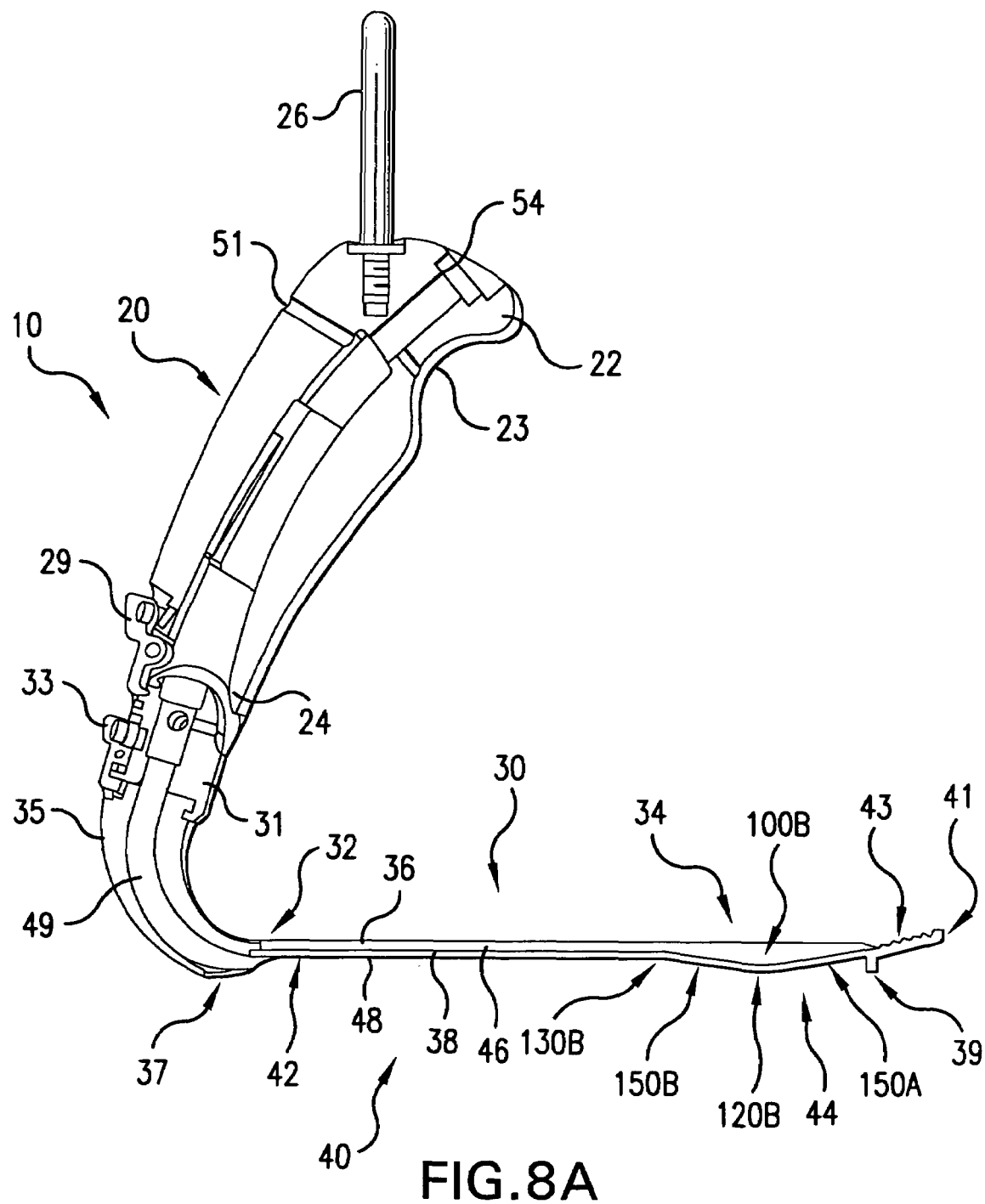
FIGS. 8A and 8B are enlarged side views of an alternate preferred form of an illuminated retractor according to the present invention with a connector at the upper end of the handle member for connecting a standard optical cable to a short optical cable in the handle member, and wherein the first elongate section includes a flanged/winged portion.
Figure 8B:
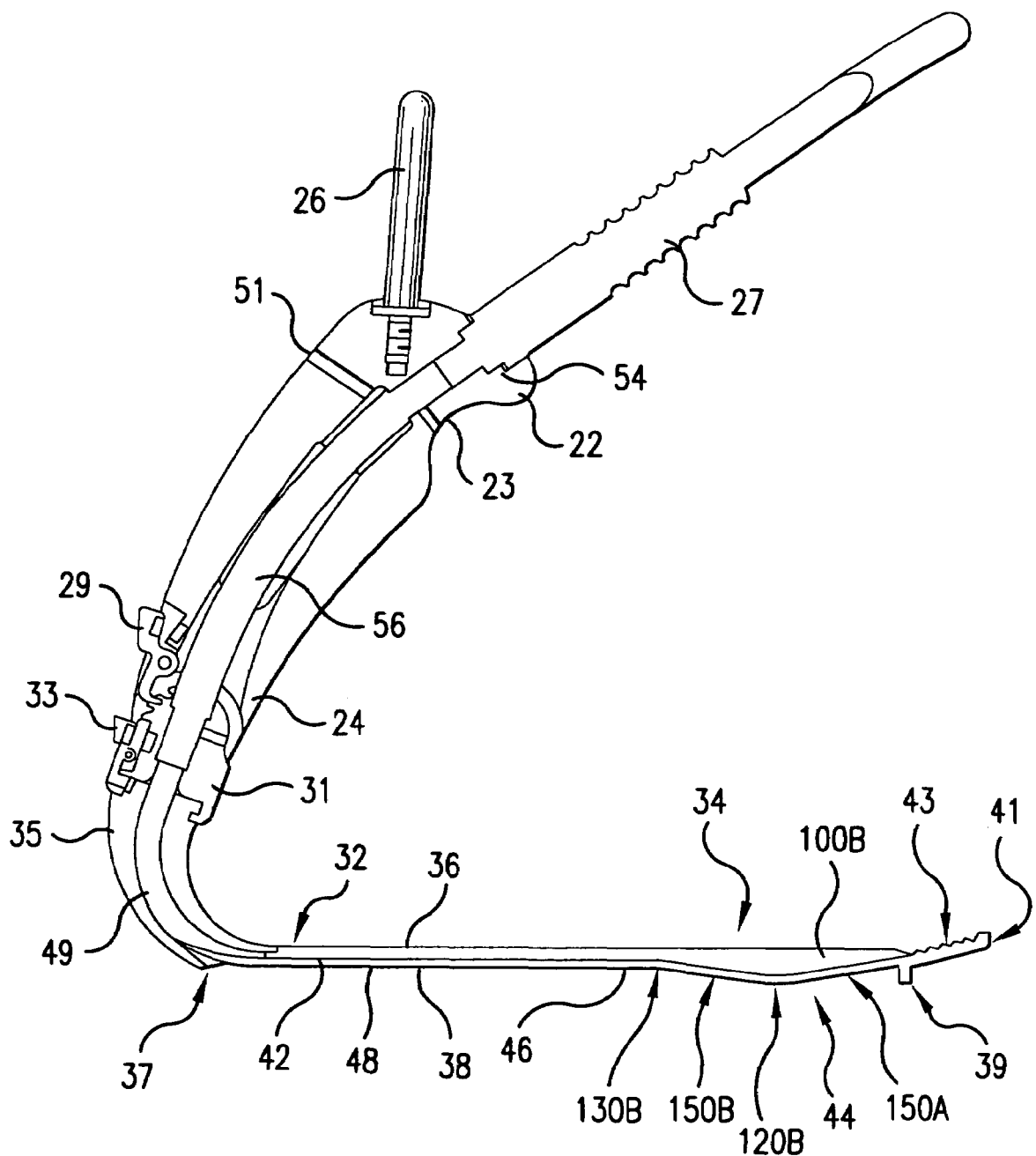

In an alternate, yet preferred embodiment shown in FIGS. 8A and 8B, the light energy passes from the light source, through the optical cable 27, to the second connector 54 and into the short cable 56. From the short cable 56, the light energy passes to the twist connector 31 and into the shaft shaped member 49 of the second elongate section 30.

The shaft shaped member 49 of the second elongate section 40 directs the illumination to the second elongate distal end portion 42 of the second elongate section 40, and allows light energy to enter the second elongate section 40. The light energy fills the second elongate section 40 and is radiated therefrom, particularly from the inner surface 48 of the second elongate section 40 between the distal end portion 42 and proximal end portion 44 of the second elongate section, and preferably from the chamfered surface 52 (if included) on the proximal end portion 44 of the second elongate section.

The light is then directed into the subcutaneous space defined/exposed by the retractor 10. Since substantially the entire length of the second elongate section 40 is illuminated, a large, well-illuminated surgical field extends the substantial length of the second elongate section 40 of the retractor 10. This allows medical personnel to visualize tissue and, ultimately, the vessel (e.g., the saphenous vein) to be harvested. Such visualization is achieved in a minimally invasive manner, and without the need for viewing the surgical field through endoscopic visual devices.

The twist connector 31 couples the optical cable 27 to the shaft shaped member 49 of the second elongate section 40. The twist connector 31 is adapted to receive and releasably retain the shaft portion 35 of the first elongate section and the shaft shaped member 49 of the second elongate section therein to couple the shaft shaped member 49 to the optical cable 27, and to connect the first elongate section to the handle member 20. In this manner, light can be provided from the light source via the optical cable 27 to the shaft shaped member 49 of the second elongate section 40 so that the second elongate section 40 is illuminated.

Referring further to the drawings, the proximal tip 41 of the first elongate section 30 preferably has a rounded shape or a smoothly-radiused, pointed shape that allows the retractor 10 to be pushed into the small, transverse incision(s) made by medical personnel, and to be maneuvered through tissue within the subcutaneous space.

The tip 41 preferably has an outer surface that includes a plurality of dissecting serrations 43 thereon. Each of these serrations 43 is preferably oriented at a substantial right angle to the lengthwise dimension of the upper proximal portion of the tip 41.

It is contemplated that the serrations 43 may be placed at an angle, other than the right angle described above, relative to the upper proximal portion of the tip 41. It is also contemplated that the serrations 43 might be placed at a series of angles to form a graphic series of serrations 43 (e.g., a plurality of arrow, or v-shaped, serrations 43 with the point of the arrow oriented toward the proximal end portion 34 of the first elongate section 40) to increase the tissue gripping ability of his portion of the retractor 10.

One purpose of tip 41 is to assist medical personnel translate some of the applied force to the retractor 10 into a dissecting force by letting the tip 41, with the dissecting serrations 43, perform some of the required dissecting work. By using the retractor 10 to accomplish some of the dissecting required by the vessel harvesting procedure, medical personnel can, while still performing the procedure in a less invasive manner, more rapidly complete the surgical procedure, thus resulting in reduced surgical time, and a reduced possibility of trauma to the patient from the surgery.

The present invention has been described in reference to use in harvesting blood vessels. It would be obvious to one skilled in the art, however, that the present invention could also be used in other minimally invasive surgical procedures in which the illumination of the minimally invasive surgical field is desired. Further, although the present invention has been described with reference to specific details of preferred embodiments thereof, it is not intended that such detail should be regarded as limiting the scope of the invention, except as and to the extent that they are included in the accompanying claims. Moreover, all documents mentioned herein are incorporated by reference herein in their entirety.

What is claimed is:

1. An illuminated surgical retractor comprising:
    a handle member having a first handle member end portion and a second handle member end portion;
    a first elongate section having length, a first elongate proximal end portion, a first elongate distal end portion, and a first elongate inner surface extending from the first elongate proximal end portion to near the first elongate distal end portion, at least a portion of the first elongate section having a substantially non uniform width, the second handle member end portion of said handle member connected to the first elongate distal end portion of said first elongate section such that said handle member forms an acute angle with said first elongate section; and
    a second elongate section having a second elongate proximal end portion, a second elongate distal end portion, and a second elongate outer surface extending from the second elongate proximal end portion to near the second elongate distal end portion, and a second elongate inner surface extending from the second elongate proximal end portion to near the second elongate distal end portion, said second elongate section connected to said first elongate section such that said first and second elongate sections are substantially parallel;

said second handle member end portion having a pivotal connector associated therewith, wherein said pivotal connector couples the first elongate section and the handle member, and wherein said second handle member end portion is adapted to optically couple the second elongate section to a source of illumination so that said second elongate section is substantially illuminated.

2. The illuminated surgical retractor of claim 1, wherein the width of the first elongate section is in the range of about 0.2 inch to 1.6 inch.

3. The illuminated surgical retractor of claim 1, wherein at least a portion of the first elongate section includes a tapered width.

4. The illuminated surgical retractor of claim 3, wherein the first elongate section includes two sides, and wherein the width of the first elongate section tapers substantially identically on each side thereof.

5. The illuminated surgical retractor of claim 3, wherein the first elongate section has an inclusive angle of taper in the range of about 1° to about 75°.

6. The illuminated surgical retractor of claim 5, wherein the inclusive angle of taper is about 9°.

7. The illuminated surgical retractor of claim 1, wherein the second elongate proximal end portion culminates in a chamfered surface at an angle in the range of about 30° to 60°.

8. An illuminated surgical retractor comprising:
a handle member having a first handle member end portion and a second handle member end portion;
a first elongate section having a first elongate proximal end portion, a first elongate distal end portion, and a first elongate inner surface extending from the first elongate proximal end portion to near the first elongate distal end portion, at least a portion of the first elongate section having a tapered width, the second handle member end portion of said handle member operatively connected to the first elongate distal end portion of said first elongate section such that said handle member forms an acute angle with said first elongate section; and
a second elongate section having a lengthwise dimension and a second elongate proximal end portion, a second elongate distal end portion and a second elongate outer surface extending from the second elongate proximal end portion to near the second elongate distal end portion, and a second elongate inner surface extending from the second elongate proximal end portion to near the second elongate distal end portion, said second elongate section defining an illumination output portion and being generally aligned with the first elongate section;
said second handle member end portion having a pivotal connector associated therewith and said pivotal connector pivotally couples the first elongate section and the handle member and said second handle member end portion is adapted to optically couple the second elongate section to a source of illumination so that said second elongate section is illuminated.

9. The illuminated surgical retractor of claim 8, wherein the first elongate section includes two sides, and wherein the width of the first elongate section tapers substantially identically on each side thereof.

10. The illuminated surgical retractor of claim 8, wherein the first elongate section includes a proximal tip, and wherein the width of the first elongate section tapers from about the proximal tip to about the first elongate distal end portion.

11. The illuminated surgical retractor of claim 10, wherein the width of the first elongate section tapers outwardly from about the proximal tip to about the first elongate distal end portion.

12. The illuminated surgical retractor of claim 8, wherein the first elongate section has an inclusive angle of taper in the range of about 1° to about 75°.

13. The illuminated surgical retractor of claim 8, wherein at least a portion of said second elongate section is surrounded by at least a portion of said first elongate section.

14. The illuminated surgical retractor of claim 8, wherein the first elongate section includes an insertion area shaped to receive at least a portion of said second elongate section therein.

15. The illuminated surgical retractor of claim 14, wherein the insertion area of the first elongate section is a substantially U-shaped flap.

16. The illuminated surgical retractor of claim 8, wherein the second elongate proximal end portion culminates in a chamfered surface at an angle in the range of about 30° to 60°.

17. An illuminated surgical retractor comprising:
a handle member having a first handle member end portion and a second handle member end portion;
a first elongate section having a first elongate proximal end portion, a first elongate distal end portion, and a first elongate inner surface extending from the first elongate proximal end portion to near the first elongate distal end portion, at least a portion of the first elongate section having a tapered width, the second handle member end portion of said handle member connected to said first elongate section such that said handle member forms an acute angle with said first elongate section;
a second elongate section having a second elongate proximal end portion, a second elongate distal end portion and a second elongate outer surface extending from the second elongate proximal end portion to near the second elongate distal end portion, and a second elongate inner surface extending from the second elongate proximal end portion to near the second elongate distal end portion, said second elongate section connected to said first elongate section such that said first and second elongate sections are substantially aligned, the second elongate distal end portion of said second elongate section defining an illumination output member; and
an insertion area on the first elongate proximal end portion for the receipt of at least a portion of the second elongate section therein.

18. The illuminated surgical retractor of claim 17, wherein the insertion area is a substantially U-shaped flap.

19. The illuminated surgical retractor of claim 17, wherein the first elongate section includes two sides, and wherein the width of the first elongate section tapers substantially identically on each side thereof.

20. The illuminated surgical retractor of claim 17, wherein the first elongate section includes a proximal tip, and wherein the width of the first elongate section tapers from about the proximal tip to about the first elongate distal end portion.

21. The illuminated surgical retractor of claim 20, wherein the width of the first elongate section tapers outwardly from about the proximal tip to about the first elongate distal end portion.

22. The illuminated surgical retractor of claim 17, wherein the first elongate section has an inclusive angle of taper in the range of about 1° to about 75°.

23. The illuminated surgical retractor of claim 17, wherein the second elongate proximal end portion culminates in a chamfered surface at an angle in the range of about 30° to 60°.

24. The illuminated surgical retractor of claim 17, wherein said handle member is operatively connected to said first elongate section by a pivotal connector.

25. The illuminated surgical retractor of claim 24, wherein said pivotal connector enables said second elongate section to be interchangeable with respect to the first elongate section.

26. An illuminated surgical retractor comprising:
   a handle member having a first handle member end portion and a second handle member end portion and at least a portion thereof that is illuminated in use;
   a first elongate section having a first elongate proximal end portion, a first elongate distal end portion, and a first elongate inner surface extending from the first elongate proximal end portion to near the first elongate distal end portion, at least a portion of the first elongate section having an outwardly tapering width, the second handle member end portion of said handle member connected to the first elongate distal end portion of said first elongate section such that said handle member is pivotal with respect thereto and forms an acute angle with said first elongate section; and
   a second elongate section having a second elongate proximal end portion, a second elongate distal end portion, and a second elongate outer surface extending from the second elongate proximal end portion to near the second elongate distal end portion, and a second elongate inner surface extending from the second elongate proximal end portion to near the second elongate distal end portion, the second elongate distal end portion of said second elongate section defining an illumination output member.

27. The illuminated surgical retractor of claim 26, wherein said second elongate section includes a shaft shaped portion that is substantially enclosed by at least a portion of said first elongate section.

28. The illuminated surgical retractor of claim 26, wherein an acute angle is formed between said handle member and said first elongate section, and wherein said acute angle is pivotal from about 30° to 95°.

29. The illuminated surgical retractor of claim 26, wherein the second elongate proximal end portion culminates in a chamfered surface at an angle in the range of about 30° to 60°.

30. The illuminated surgical retractor of claim 26, wherein the first elongate section includes a proximal tip, and wherein the width of the first elongate section outwardly tapers from about the proximal tip to about the distal end portion.

31. An illuminated surgical retractor for illuminating the subcutaneous space between a vessel and the subcutaneous tissue of a patient, the retractor comprising:
   a handle member having a first handle member end portion and a second handle member end portion with a gripping area therebetween for gripping by the user and an optical cable extending therethrough;
   an elongate first elongate section having a first elongate proximal end portion, a proximal tip, and a first elongate distal end portion with a first elongate inner surface extending between the first elongate proximal end portion and the first elongate distal end portion, at least a portion of said first elongate section having a width that tapers outwardly at an inclusive taper angle in the range of about 1° to 75°, the second handle member end portion of said handle member being connected to the first elongate section;
   a second elongate section being formed to direct light laterally therefrom, and beyond the first elongate section, the second elongate section having:
      a second elongate proximal end portion that culminates in a chamfered surface at an angle in the range of about 30° to 60°, and
      a second elongate distal end portion with a second elongate inner surface and a second elongate outer surface each extending between the second elongate proximal end portion and the second elongate distal end portion, the second elongate section further
   including an illumination input end portion thereon, wherein at least a portion of said illumination input end portion is substantially surrounded by a portion of said first elongate section;
   a connector optically coupling the illumination input end portion to the optical cable;
   a connector for connecting the handle member and the first elongate section such that the first elongate section is oriented at an acute angle relative the handle member; and
   a substantially U-shaped flap extending from the first elongate section and into which the second elongate section is insertable, wherein at least a portion of said second elongate section, once inserted into the insertion area of the first elongate section, is laterally removable therefrom.

* * * * *